United States Patent
Mensinger et al.

(10) Patent No.: US 11,437,141 B2
(45) Date of Patent: Sep. 6, 2022

(54) PERFORMANCE REPORTS ASSOCIATED WITH CONTINUOUS SENSOR DATA FROM MULTIPLE ANALYSIS TIME PERIODS

(71) Applicant: DexCom, Inc., San Diego, CA (US)

(72) Inventors: Michael Robert Mensinger, San Diego, CA (US); Deborah M. Ruppert, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 522 days.

(21) Appl. No.: 15/422,196

(22) Filed: Feb. 1, 2017

(65) Prior Publication Data
US 2017/0143251 A1 May 25, 2017

Related U.S. Application Data

(63) Continuation of application No. 12/770,618, filed on Apr. 29, 2010, now abandoned.
(Continued)

(51) Int. Cl.
G16H 50/20 (2018.01)
G16H 15/00 (2018.01)
(Continued)

(52) U.S. Cl.
CPC ........... *G16H 50/20* (2018.01); *A61B 5/0031* (2013.01); *A61B 5/14503* (2013.01);
(Continued)

(58) Field of Classification Search
None
See application file for complete search history.

(56) References Cited

U.S. PATENT DOCUMENTS

| 4,907,857 A | 3/1990 | Giuliani et al. |
| 5,462,064 A | 10/1995 | D'Angelo et al. |

(Continued)

FOREIGN PATENT DOCUMENTS

| CA | 2127172 | 7/1998 |
| EP | 0 107 634 | 5/1984 |

(Continued)

OTHER PUBLICATIONS

Biermann et al. 2008. How would patients behave if they were continually informed of their blood glucose levels? A simulation study using a "virtual" patient. Diabetes Technology & Therapeutics 10:178-187.

(Continued)

*Primary Examiner* — Soren Harward
(74) *Attorney, Agent, or Firm* — Patterson + Sheridan, LLP

(57) ABSTRACT

A method of providing performance reports to persons associated with the monitoring of an analyte level, such as blood glucose concentrations in a host, is provided. The performance reports can indicate a measure of an analyte variability of the host over a first analysis time period compared to a measure of analyte variability of the host over one or more other analysis time periods. The analyte level of the host can be received in each of a plurality of sensor readings from a continuous analyte sensor, such as multiple sensor readings per hour, so that the analyte variability that is used in determining the performance report of the host can be based on not just a few metered readings taken by the host, but a plurality of intermittent readings that are taken by a continuous analyte sensor, for example. Various types of performance reports can be generated, such as reports that comprise charts, graphs, tables, and/or other visual indicia of
(Continued)

a host's performance during one analysis period versus another analysis period.

11 Claims, 11 Drawing Sheets

Related U.S. Application Data

(60) Provisional application No. 61/174,436, filed on Apr. 30, 2009.

(51) Int. Cl.
*A61B 5/00* (2006.01)
*A61B 5/145* (2006.01)

(52) U.S. Cl.
CPC ...... *A61B 5/14532* (2013.01); *A61B 5/14546* (2013.01); *A61B 5/486* (2013.01); *A61B 5/681* (2013.01); *A61B 5/7275* (2013.01); *A61B 5/743* (2013.01); *G16H 15/00* (2018.01); *A61B 2560/045* (2013.01)

(56) References Cited

U.S. PATENT DOCUMENTS

| | | | |
|---|---|---|---|
| 5,497,772 A * | 3/1996 | Schulman | A61B 5/14865 600/347 |
| 5,640,470 A | 6/1997 | Iyer et al. | |
| 5,928,155 A | 7/1999 | Eggers et al. | |
| 6,001,067 A | 12/1999 | Shults et al. | |
| 6,325,978 B1 | 12/2001 | Labuda et al. | |
| 6,330,464 B1 | 12/2001 | Colvin, Jr. et al. | |
| 6,424,847 B1 | 7/2002 | Mastrototaro et al. | |
| 6,477,395 B2 | 11/2002 | Schulman et al. | |
| 6,484,046 B1 | 11/2002 | Say et al. | |
| 6,512,939 B1 | 1/2003 | Colvin et al. | |
| 6,565,509 B1 | 5/2003 | Say et al. | |
| 6,572,545 B2 | 6/2003 | Knobbe et al. | |
| 6,574,490 B2 | 6/2003 | Abbink et al. | |
| 6,575,905 B2 | 6/2003 | Knobbe et al. | |
| 6,579,690 B1 | 6/2003 | Bonnecaze et al. | |
| 7,025,743 B2 | 4/2006 | Mann et al. | |
| 7,647,237 B2 | 1/2010 | Malave et al. | |
| 2002/0099282 A1 | 7/2002 | Knobbe et al. | |
| 2002/0111547 A1 | 8/2002 | Knobbe et al. | |
| 2002/0193679 A1 | 12/2002 | Malave et al. | |
| 2003/0235817 A1 | 12/2003 | Bartkowiak et al. | |
| 2005/0027463 A1 | 2/2005 | Goode et al. | |
| 2005/0038332 A1 * | 2/2005 | Saidara | A61B 5/0002 600/347 |
| 2005/0143635 A1 | 6/2005 | Kamath et al. | |
| 2005/0143675 A1 | 6/2005 | Neel et al. | |
| 2005/0215871 A1 | 9/2005 | Feldman et al. | |
| 2006/0036141 A1 | 2/2006 | Kamath et al. | |
| 2006/0095225 A1 * | 5/2006 | Harmon | G16H 50/20 702/127 |
| 2007/0083564 A1 | 4/2007 | Ramacher et al. | |
| 2007/0179352 A1 * | 8/2007 | Randlov | G16H 20/17 600/300 |
| 2007/0232876 A1 | 10/2007 | Otto et al. | |
| 2008/0071157 A1 | 3/2008 | McGarraugh et al. | |
| 2008/0071158 A1 | 3/2008 | McGarraugh et al. | |
| 2008/0072663 A1 | 3/2008 | Keenan et al. | |
| 2008/0154513 A1 * | 6/2008 | Kovatchev | G06F 19/3456 702/19 |
| 2008/0288180 A1 * | 11/2008 | Hayter | A61B 5/0008 702/23 |
| 2008/0306353 A1 | 12/2008 | Douglas et al. | |
| 2009/0030382 A1 | 1/2009 | Brandt | |
| 2010/0095229 A1 | 4/2010 | Dixon et al. | |
| 2011/0004085 A1 | 1/2011 | Mensinger et al. | |

FOREIGN PATENT DOCUMENTS

| | | |
|---|---|---|
| EP | 0 288 793 | 11/1988 |
| EP | 0 352 610 | 1/1990 |
| EP | 0 352 631 | 1/1990 |
| EP | 0 406 473 | 1/1991 |
| EP | 0 440 044 | 8/1991 |
| EP | 0 441 252 A2 | 8/1991 |
| EP | 0 467 078 A2 | 1/1992 |
| EP | 0 323 605 B1 | 1/1994 |
| EP | 0 647 849 | 4/1995 |
| EP | 0 424 633 | 1/1996 |
| EP | 1 153 571 | 11/2001 |
| EP | 2006786 A1 | 12/2008 |
| EP | 2 226 086 | 8/2010 |
| EP | 2 223 710 | 9/2010 |
| WO | WO 1990-07575 | 7/1990 |
| WO | WO 1990-10861 | 9/1990 |
| WO | WO 1992-08979 | 5/1992 |
| WO | WO 1992-12255 | 7/1992 |
| WO | WO 1992-13271 | 8/1992 |
| WO | WO 1992-15701 | 9/1992 |
| WO | WO 1992-15704 | 9/1992 |
| WO | WO 1992-15863 | 9/1992 |
| WO | WO 1992-21769 | 12/1992 |
| WO | WO 1992-21770 | 12/1992 |
| WO | WO 1992-21772 | 12/1992 |
| WO | WO 1992-21975 | 12/1992 |
| WO | WO 1992-21980 | 12/1992 |
| WO | WO 1993-07298 | 4/1993 |
| WO | WO 1993-20060 | 10/1993 |
| WO | WO 1993-20444 | 10/1993 |
| WO | WO 1993-21346 | 10/1993 |
| WO | WO 1994-01531 | 1/1994 |
| WO | WO 1994-10258 | 5/1994 |
| WO | WO 1995-23973 | 9/1995 |
| WO | WO 1995-25282 | 9/1995 |
| WO | WO 1995-33206 | 10/1995 |
| WO | WO 1996-14026 | 5/1996 |
| WO | WO 1996-32004 | 10/1996 |
| WO | WO 1996-41179 | 12/1996 |
| WO | WO 1996-41187 | 12/1996 |
| WO | WO 1998-19159 | 5/1998 |
| WO | WO 1998-38906 | 9/1998 |
| WO | WO 1999-09410 | 2/1999 |
| WO | WO 1999-56613 | 4/1999 |
| WO | WO 1999-23230 | 5/1999 |
| WO | WO 1999-58051 | 11/1999 |
| WO | WO 2000-013002 | 3/2000 |
| WO | WO 2000-013003 | 3/2000 |
| WO | WO 2000-032098 | 6/2000 |
| WO | WO 2001-016579 | 3/2001 |
| WO | WO 2001-020334 | 3/2001 |
| WO | WO 2001-052727 | 7/2001 |
| WO | WO 2001-088534 | 11/2001 |
| WO | WO 2002-024065 | 3/2002 |
| WO | WO 2002-082989 | 10/2002 |
| WO | WO 2002-089666 | 11/2002 |
| WO | WO 2003-101862 | 12/2003 |
| WO | WO 2004-110256 | 12/2004 |
| WO | WO 2005-032400 | 4/2005 |
| WO | WO 2005-078424 | 8/2005 |
| WO | WO 2005-093629 | 10/2005 |
| WO | WO 2005/093629 | 10/2005 |
| WO | WO 2006-050405 | 5/2006 |
| WO | WO 2006-118713 | 11/2006 |
| WO | WO 2006-131288 | 12/2006 |
| WO | WO 2007-002579 | 1/2007 |
| WO | WO 2007/005170 | 1/2007 |
| WO | WO 2007-005170 | 1/2007 |
| WO | WO 2007-065285 | 6/2007 |
| WO | WO 2007-114943 | 10/2007 |
| WO | WO 2007-127606 | 11/2007 |

(56) References Cited

FOREIGN PATENT DOCUMENTS

| WO | WO 2007-143225 | 12/2007 |
|----|----------------|---------|
| WO | WO 2008-076868 | 6/2008  |

OTHER PUBLICATIONS

Bobbioni-Harsch et al. 1993. Lifespan of subcutaneous glucose sensors and their performances during dynamic glycaemia changes in rats. J Biomed Eng 15:457-463.
Bremer et al. 1999. Is blood blucose predictable from previous values? A solicitation for data. Diabetes 48:445-451.
Bremer et al. 2001. Benchmark data from the literature for evaluation of new glucose sensing technologies. Diabetes Technology & Therapeutics 3(3):409-418.
Cass et al. 1984. Ferrocene-mediated enzyme electrodes for amperometric determination of glucose. Analytical Chemistry 36:667-671.
CLSI. 2008. Performance metrics for continuous interstitial glucose monitoring; approved guideline CLSI document POCT05-A. Wayne PA: Clinical and Laboratory Standards Institute. 28(33) (72 pages).
DuPont$^I$ Dimension AR® (Catalog) 1998.
Fabietti et al. 2007. Clinical validation of a new control-oriented model of insulin and glucose dynamics in subjects with type 2 diabetes. Diabetes Technology & Therapeutics 9(4):327-338.
Gerritsen et al. 1999. Performance of subcutaneously implanted glucose sensors for continuous monitoring. The Netherlands Journal of Medicine 54:167-179.
Gross et al. 2000. Efficacy and reliability of the continuous glucose monitoring system. Diabetes Technology & Therapeutics 2(Suppl 1):S19-S26.
Guerci et al. 2003. Clinical performance of CGMS in type 1 diabetic patients treated by continuous subcutaneous insulin infusion using insulin analogs. Diabetes Care 26:582-589.
Harrison et al. 1988. Characterization of perfluorosulfonic acid polymer coated enzyme electrodes and a miniaturized integrated potentiostat for glucose analysis in whole blood. Analytical Chemistry 60:2002-2007.
Hitchman M. L. 1978. Measurement of Dissolved Oxygen. In Elving et al. (Eds.) . . . New York; John Wiley & Sons. Chemical Analysis vol. 49, Chap. 3 pp. 34-49, 59-123.
Ishikawa et al. 1998. Initial evaluation of a 290-mm diameter subcutaneous glucose sensor: Glucose monitoring with a biocompatible flexible-wire enzyme-based amperometric.
Johnson et al. 1992. In vivo evaluation of an electroenzymatic glucose sensor implanted in subcutaneous tissue, Biosensors & Bioelectronics 7:709-714.
Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.
Madaras et al. 1996. Microfabricated arnperometric creatine and creatinine biosensors. Analytica Chimica Acta 319:335-345.
Makale et al. 2003. Tissue window chamber system for validation of implanted oxygen sensors. Am J Physiol Heart Circ Physiol 284:H2288-2294.
Neuburger et al. 1987. Pulsed arnperometric detection of carbohydrates at gold electrodes with a two-step potential waveform. Anaytical Chemistry 59:150-154.
Panteleon et al. 2003. The role of the independent variable to glucose sensor calibration. Diabetes Technology & Therapeutics 5(3):401-410.
Pickup et al. 1987/88. Implantable glucose sensors: choosing the appropriate sensing strategy. Biosensors 3:335-346.
Rabah et al. 1991. Electrochemical wear of graphite anodes during electrolysis of brine. Carbon 29(2):165-171.
Rigla et al. 2008. Real-time continuous glucose monitoring together with telernedical assistance improves glycemic control and glucose stability in pump-treated patients. Diabetes Technology & Therapeutics 10:194-199.
Schuler et al. 1999. Modified gas-permeable silicone rubber membranes for covalent immobilisation of enzymes and their use in biosensor development. Analyst 124:1181-1184.
Service et al. 1970. Mean amplitude of glycemic excursions a measure of diabetic instability. Diabetes 19: 644-655.
Sparacino et al. 2008. Continuous glucose monitoring time series and hypo/hyperglycemia prevention: requirements methods open problems. Current Diabetes Reviews 4:181-192.
Sternberg et al. 1988. Covalent enzyme coupling on cellulose acetate membranes for glucose sensor development. Analytical Chemistry 69:2781-2786.
Updike et al. 2000. A subcutaneous glucose sensor with improved longevity dynamic range and stability of calibration. Diabetes Care 23(2):208-214.
Ward et al. 2000. Understanding Spontaneous Output Fluctuations of an Amperometric Glucose Sensor: Effect of Inhalation Anesthesia and use of a Nonenzyme Containing Electrode. ASAIO Journal 46:540-546.
Zhu et al. 2002. Planar amperometric glucose sensor based on glucose oxidase immobilized by chitosan film on prussian blue layer. Sensors 2:127-136.
PCT/US2010/003045, filed Apr. 29, 2010: International Preliminary Report on Patentability and Written Opinion dated Nov. 1, 2011.
PCT/US2010/003045, filed Apr. 29, 2010: International Search Report dated Dec. 10, 2010.
Extended European Search Report for Application No. 10770372.0 dated May 21, 2013, 6 pages.
International Preliminary Report on Patentability for Application No. PCT/US2010/033045 dated Nov. 10, 2011, 5 pages.
International Search Report and Written Opinion for Application No. PCT/US2010/033045 dated Dec. 10, 2010, 10 pages.
Office Action from European Patent Application No. 10770372.0, dated Dec. 15, 2020, 54 pages.
Monnier L., et al., "Glycemic Variability: The Third Component of the Dysglycemia in Diabetes. Is It Important? How to Measure It?" Journal of the Diabetes Science and Technology, Nov. 6, 2008, vol. 2, Issue 6, XP055852232, retrieved on Oct. 18, 2021, pp. 1094-1100.

\* cited by examiner

|     | 29 Jan - 27 Feb 07 | 28 Feb - 27 Mar 07 | Change |     |
| --- | --- | --- | --- | --- |
| A1c % | 0.0 % | 0.0 % | N/A |     |
| Mean Glucose | 186 | 177 | -5 % | ☺ |
| Standard Deviation | 88 | 90 | 2 % | ⚠ |
| % in Hypoglycemia (39-52 mg/dL) | 1 | 2 | 100 % | ⚠ |
| % in Target (52-96 mg/dL) | 17 | 22 | 29 % | ☺ |
| % in High (96-240 mg/dL) | 53 | 49 | -8 % | ☺ |
| % in Hyperglycemia (240-401 mg/dL) | 29 | 26 | -10 % | ☺ |
|     |     |     |     |     |
| Days Sensor Used | 6 | 22 | 267 % | ☺ |

FIG. 5

| | 12 am | 1 am | 2 am | 3 am | 4 am | 5 am | 6 am | 7 am | 8 am | 9 am | 10 am | 11 am |
|---|---|---|---|---|---|---|---|---|---|---|---|---|
| 29 Jan - 27 Feb | 214 | 145 | 140 | 152 | 205 | 202 | 209 | 193 | 166 | 217 | 222 | 241 |
| 28 Feb - 27 Mar | 180 | 190 | 171 | 149 | 170 | 180 | 189 | 177 | 161 | 150 | 159 | 177 |

| | 12 pm | 1 pm | 2 pm | 3 pm | 4 pm | 5 pm | 6 pm | 7 pm | 8 pm | 9 pm | 10 pm | 11 pm |
|---|---|---|---|---|---|---|---|---|---|---|---|---|
| 29 Jan - 27 Feb | 182 | 147 | 212 | 181 | 160 | 173 | 186 | 169 | 168 | 133 | 204 | 225 |
| 28 Feb - 27 Mar | 185 | 180 | 173 | 178 | 178 | 178 | 179 | 197 | 193 | 185 | 188 | 180 |

PERFORMANCE REPORTS ASSOCIATED WITH CONTINUOUS SENSOR DATA FROM MULTIPLE ANALYSIS TIME PERIODS

Any and all priority claims identified in the Application Data Sheet, or any correction thereto, are hereby incorporated by reference under 37 CFR 1.57. This application is a continuation of U.S. application Ser. No. 12/770,618, filed Apr. 29, 2010, which claims the benefit under 35 U.S.C. § 119(e) of U.S. Provisional Application No. 61/174,436, filed Apr. 30, 2009. Each of the aforementioned applications is incorporated by reference herein in its entirety, and each is hereby expressly made a part of this specification.

FIELD OF THE INVENTION

Systems and methods for providing performance reports to persons with diabetes that generally indicate a measure of a glucose variability of the person over multiple analysis time periods are provided.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which may cause an array of physiological derangements (for example, kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes will normally only measure his or her glucose levels two to four times per day. Unfortunately, these time intervals are so far apart that the person with diabetes will likely find out too late about hyper- or hypo-glycemic conditions. In fact, it is not only unlikely that a person with diabetes will take a timely SMBG value, it is likely that the person with diabetes will not know if their blood glucose value is going up (higher) or down (lower) based on conventional methods. Thus, their ability to make educated insulin therapy decisions is inhibited.

Some attempts have been made to continuously measure the glucose concentration in a person with diabetes. More frequent measurements can allow the person with diabetes to know of essentially current blood sugar conditions and to make appropriate decisions in response to the current conditions.

SUMMARY OF THE INVENTION

In a first aspect, a method of analyzing continuous analyte sensor data associated with a host is provided, wherein the continuous analyte sensor data is representative of glucose levels of the host, the method comprising: accessing a plurality of blood glucose readings associated with a host during two or more analysis time periods, wherein each blood glucose reading is indicative of a blood glucose level of the host at a respective time; and generating a performance report indicating a relationship between the plurality of blood glucose readings of the two or more analysis time periods, wherein the performance report is indicative of glucose control by the host over the two or more analysis time periods.

In an embodiment of the first aspect, the performance report further indicates a relationship between the plurality of blood glucose readings of the two or more analysis time periods and target sensor data.

In an embodiment of the first aspect, the method further comprises initiating transmission of appropriate clinical feedback to the host in response to determining that the relationship between the plurality of blood glucose readings meets criteria indicative of providing the host with clinical feedback.

In an embodiment of the first aspect, the plurality of blood glucose readings comprises more than 72 blood glucose readings for each 24 hour period of an at least one week period.

In an embodiment of the first aspect, the method further comprises transmitting the performance report to a caretaker computing device.

In a second aspect, a method of analyzing continuous analyte sensor data associated with a host is provided, wherein the continuous analyte sensor data is representative of glucose levels of the host, the method comprising: receiving from a user an indication of a first starting date of a first analysis time period; determining a first ending date of the first analysis time period by adding a predetermined time period to the first starting date; determining a second starting date of a second analysis time period; determining a second ending date of the second analysis time period by adding the predetermined time period to the second starting date; accessing a plurality of blood glucose levels associated with a host during the first analysis time period and the second analysis time period, wherein each blood glucose level is indicative of a blood glucose level of the host at respective times; determining one or more first statistical values associated with the first analysis time period based on each of the blood glucose levels of the host received during the first analysis time period; determining one or more second statistical values associated with the second analysis time period based on each of the blood glucose levels of the host received during the second analysis time period; and determining a comparison indicator indicating a relationship between the first one or more statistical values and the second one or more statistical values.

In an embodiment of the second aspect, the second starting data of the second analysis time period is a day that immediately follows the first ending date.

In an embodiment of the second aspect, the one or more first statistical values comprise a first mean glucose level of the blood glucose levels received during the first analysis time period.

In an embodiment of the second aspect, the one or more second statistical values comprise a second mean glucose level of the blood glucose levels received during the second analysis time period.

In an embodiment of the second aspect, the comparison indicator indicates at least a percentage difference between the first mean glucose level and second mean glucose level.

In a third aspect, a method of analyzing continuous analyte sensor data associated with a host is provided, wherein the continuous analyte sensor data is representative of glucose levels of the host, the method comprising: intermittently receiving analyte sensor data from one or more analyte sensors associated with a host at each of a plurality of sample times; determining a plurality of blood glucose levels of the host at each of the plurality of sample times, wherein the blood glucose levels are based on at least respective analyte sensor data; storing the plurality of blood glucose levels on a storage device; accessing at least the blood glucose levels associated with the host during a first analysis time period and a second analysis time period; determining a first mean glucose level of the host during the first analysis time period, wherein the first mean glucose level is based on each of the blood glucose levels of the host received during the first analysis time period; determining a second mean glucose level of the host during the second analysis time period, wherein the second mean glucose level is based on each of the blood glucose levels of the host received during the second analysis time period; and determining at least a percentage difference between the first mean glucose level of the host during the first analysis time period and the second mean glucose level of the host during the second analysis time period.

In an embodiment of the third aspect, the predetermined time period is selected from the group consisting of 1 week, 1 month, 2 months, 3 months, 4 months, 5 months, 6 months, 9 months, and 1 year.

In an embodiment of the third aspect, the first analysis time period and the second analysis time period each comprise substantially a quarter of a year.

In an embodiment of the third aspect, the predetermined time period is indicated by the user.

In a fourth aspect, a computerized method of generating a performance report associated with continuous analyte sensor data is provided, the method configured for execution by a computing device having one or more processors, the method comprising: accessing historical sensor data associated with a host, wherein the historical sensor data comprises more than 72 blood glucose readings for each 24 hour period of an at least one week period; selecting blood glucose data associated with a first time period; determining a first statistical value that is indicative of blood glucose levels during the first time period; selecting blood glucose data associated with a second time period; determining a second statistical value that is indicative of blood glucose levels during the second time period; determining a performance indicator indicating a comparison between the first indicator and the second indicator; and generating a user interface for display on a computing device, the user interface including at least the performance indicator.

In an embodiment of the fourth aspect, the first indicator and second indicator indicate one or more items selected from the group consisting of mean glucose levels over the respective time periods, standard deviation of glucose levels over the respective time periods, percentage of days in the respective time period in which the means glucose levels were within a predefined target range, and days within the respective time periods in which blood glucose data was received from the continuous analyte sensor.

In a fifth aspect, a system for generating performance reports associated continuous analyte sensor data is provided, comprising: a computer-implemented user interface configured to receive performance report generation instructions from a user; a data storage module configured to store continuous analyte sensor data indicative of one or more analyte levels of a host; and a performance report module communicatively coupled to the user interface and the data storage module and configured to: (i) receive continuous sensor analyte data from the data storage module; (ii) determine a performance indication based on an analysis of the retrieved continuous analyte sensor data; (iii) generate a performance report based on performance report generation instructions received from the user interface and the performance indication; and (iv) transmit the generated performance report to the user interface, wherein the user interface is additionally configured to display the generated performance report.

In an embodiment of the fifth aspect, the system further comprises a continuous analyte sensor configured to generate the continuous sensor analyte data and transmit the continuous sensor analyte data to the data storage module.

In an embodiment of the fifth aspect, the system further comprises a computing device incorporating the user interface and performance report module.

In an embodiment of the fifth aspect, the computing device includes functionality of a device selected from the group consisting of a mobile telephone, a personal digital assistant, a personal computer, a smart phone, a digital media player, an exercise monitoring device, and geographic position-tracking device.

In an embodiment of the fifth aspect, the performance report generation instructions include a first analysis time period and a second analysis time period.

In an embodiment of the fifth aspect, the performance report module is additionally configured to determine a first statistical value based on continuous sensor analyte data associated with the first analysis time period, and a second statistical value based on continuous sensor analyte data associates with the second analysis time period, wherein the performance indication is based on a comparison of the first statistical value and the second statistical value.

In an embodiment of the fifth aspect, the performance report generation instructions include a first analysis time period and target sensor data.

In an embodiment of the fifth aspect, the performance report module is additionally configured to determine a first statistical value based on continuous sensor analyte data associated with the first analysis time period, wherein the performance indication is based on a comparison of the first statistical value and the target sensor data.

In an embodiment of the fifth aspect, the performance module is additionally configured to determine when a pre-defined criteria associated with the therapy recommendation is met and initiate display of the therapy recommendation on the user interface when the performance module determines that the pre-defined criteria is met.

BRIEF DESCRIPTION OF THE DRAWINGS

Various embodiments of the present invention are described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

FIGS. 5-8 illustrate exemplary performance reports that include statistical values and performance indicators in accordance with various embodiments.

DETAILED DESCRIPTION OF THE PREFERRED EMBODIMENT

Figure 1:
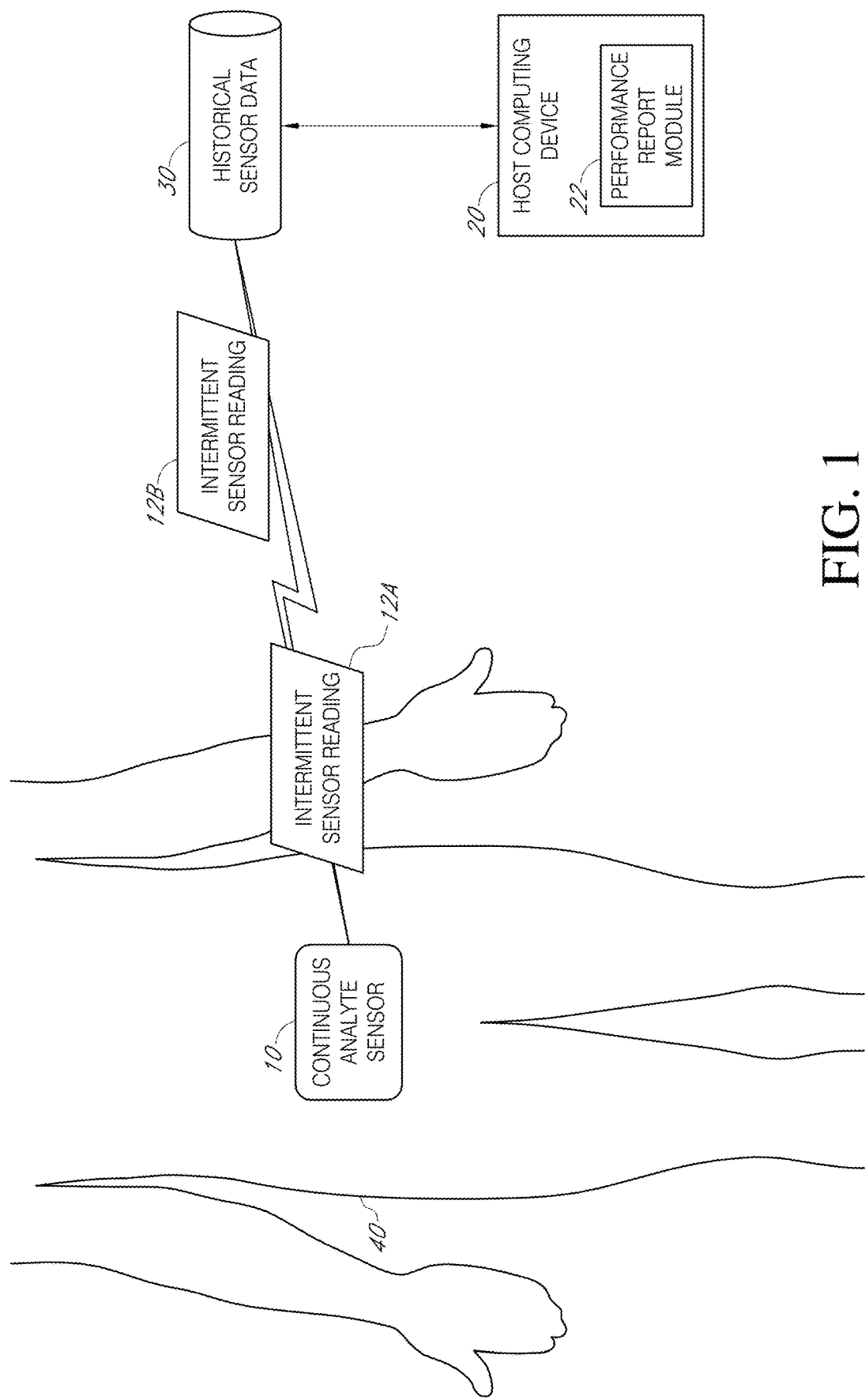
FIG. 1 is a schematic diagram of a performance report system using a host computing device in accordance with one embodiment.

In the following description of exemplary embodiments, reference is made to the accompanying drawings which form a part hereof, and in which it is shown by way of illustration specific embodiments in which the invention can be practiced. It is to be understood that other embodiments can be used and structural changes can be made without departing from the scope of the invention.

Definitions of Certain Terms

Below are definitions of certain terms.

The term "analyte" as used herein is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products.

The term "continuous analyte sensor" as used herein is a broad term, and is to be given its ordinary and customary meaning to a person of ordinary skill in the art (and is not to be limited to a special or customized meaning), and refers without limitation to a device that continuously or continually measures a concentration of an analyte, for example, at time intervals ranging from fractions of a second up to, for example, 1, 2, or 5 minutes, or longer. In one exemplary embodiment, the continuous analyte sensor is a glucose sensor such as described in U.S. Pat. No. 6,001,067, which is incorporated herein by reference in its entirety.

The term "host" as used herein is a broad term, and is to be given its ordinary and customary meaning to a person of ordinary skill in the art (and is not to be limited to a special or customized meaning), and refers without limitation to a mammal, such as a human implanted with a device.

The term "sensor data" as used herein is a broad term, and is to be given its ordinary and customary meaning to a person of ordinary skill in the art (and is not to be limited to a special or customized meaning), and refers without limitation to any data associated with a sensor, such as a continuous analyte sensor. Sensor data includes sensor readings, such as from a raw data stream, or simply data stream, of an analog or digital signal directly related to a measured analyte from an analyte sensor (or other signal received from another sensor), as well as calibrated and/or filtered raw data. In one example, the sensor readings comprise digital data in "counts" converted by an A/D converter from an analog signal (e.g., voltage or amps) and each sensor reading includes one or more data points representative of a glucose concentration. Thus, the terms sensor reading refers generally to a digital representation of sensor data (e.g. a blood glucose level) at a particular time. The term broadly encompasses a plurality of time spaced data points from a sensor, such as a from a substantially continuous glucose sensor, which comprises individual measurements taken at time intervals ranging from fractions of a second up to, e.g., 1, 2, or 5 minutes or longer. In another example, the sensor data includes an integrated digital value representative of one or more data points averaged over a time period. Sensor data may include calibrated data, smoothed data, filtered data, transformed data, and/or any other data associated with a sensor.

The term "transformed sensor data" as used herein is a broad term, and is to be given its ordinary and customary meaning to a person of ordinary skill in the art (and is not to be limited to a special or customized meaning), and refers without limitation to any data that is derived, either fully or in part, from sensor readings from one or more sensors. For example, sensor readings over a time period (e.g., 5 minutes) may be processed in order to generated transformed sensor data including one or more trend indicators (e.g., a 5 minute trend). Other examples of transformed data include filtered sensor data (e.g., one or more filtered analyte concentration values), calibrated sensor data (e.g., one or more calibrated analyte concentration values), rate of change information, trend information, rate of acceleration information, sensor diagnostic information, location information, alarm/alert information, calibration information, and/or the like.

The term "calibration" as used herein is a broad term, and is to be given its ordinary and customary meaning to a person of ordinary skill in the art (and is not to be limited to a special or customized meaning), and refers without limitation to a process of determining a relationship between sensor data and corresponding reference data, which can be used to convert sensor data into calibrated data (defined below). In some embodiments, such as continuous analyte sensors, for example, calibration can be updated or recalibrated over time as changes in the relationship between the sensor data and reference data occur, for example, due to changes in sensitivity, baseline, transport, metabolism, and the like.

The terms "calibrated data" and "calibrated data stream" as used herein are broad terms, and are to be given their ordinary and customary meaning to a person of ordinary skill in the art (and are not to be limited to a special or customized meaning), and refer without limitation to data that has been transformed from its raw state to another state using a function, for example a conversion function, to provide a meaningful value to a user.

The terms "smoothed data" and "filtered data" as used herein are broad terms, and are to be given their ordinary and customary meaning to a person of ordinary skill in the art (and are not to be limited to a special or customized meaning), and refer without limitation to data that has been modified to make it smoother and more continuous and/or to remove or diminish outlying points, for example, by performing a moving average sensor readings. Examples of data filters include FIR (finite impulse response), IIR (infinite impulse response), moving average filters, and the like.

The terms "smoothing" and "filtering" as used herein are broad terms, and are to be given their ordinary and customary meaning to a person of ordinary skill in the art (and are not to be limited to a special or customized meaning), and refer without limitation to a mathematical computation that attenuates or normalizes components of a signal, such as reducing noise errors in a raw data stream. In some embodiments, smoothing refers to modification of a data stream to make it smoother and more continuous or to remove or diminish outlying data points, for example, by performing a moving average a stream of sensor readings.

The term "time period" as used herein is a broad term, and is to be given its ordinary and customary meaning to a person of ordinary skill in the art (and is not to be limited to a special or customized meaning), and refers without limitation to an amount of time including a single point in time and a path (for example, range of time) that extends from a first point in time to a second point in time.

The term "measured analyte values" as used herein is a broad term, and is to be given its ordinary and customary meaning to a person of ordinary skill in the art (and is not to be limited to a special or customized meaning), and refers without limitation to an analyte value or set of analyte values for a time period for which analyte data has been measured by an analyte sensor. The term is broad enough to include data from the analyte sensor before or after data processing in the sensor and/or receiver (for example, data smoothing, calibration, or the like).

The term "estimated analyte values" as used herein is a broad term, and is to be given its ordinary and customary meaning to a person of ordinary skill in the art (and is not to be limited to a special or customized meaning), and refers without limitation to an analyte value or set of analyte values, which have been algorithmically extrapolated from measured analyte values. Typically, estimated analyte values are estimated for a time period during which no data exists. However, estimated analyte values can also be estimated during a time period for which measured data exists, but is to be replaced by algorithmically extrapolated data due to a time lag in the measured data, for example.

The term "alarm" as used herein is a broad term, and is to be given its ordinary and customary meaning to a person of ordinary skill in the art (and is not to be limited to a special or customized meaning), and refers without limitation to audible, visual, or tactile signals that are triggered in response to detection of clinical risk to a patient. In one embodiment, hyperglycemic and hypoglycemic alarms are triggered when present or future clinical danger is assessed based on continuous analyte data.

The terms "target analyte values" and "analyte value goal" as used herein are broad terms, and are to be given their ordinary and customary meaning to a person of ordinary skill in the art (and are not to be limited to a special or customized meaning), and refer without limitation to an analyte value or set of analyte values that are clinically acceptable. In one example, a target analyte value is visually or audibly presented to a patient in order to aid in guiding the patient in understanding how they should avoid a clinically risky analyte concentration.

The term "module" as used herein is a broad term, and is to be given its ordinary and customary meaning to a person of ordinary skill in the art (and is not to be limited to a special or customized meaning), and refers without limitation to software, firmware, hardware, and any combination of these elements for performing the associated functions described herein. Additionally, for purpose of discussion, the various modules are described from time-to-time as discrete modules; however, as would be apparent to one of ordinary skill in the art, two or more modules may be combined to form a single module that performs the associated functions according embodiments.

The terms "computer program product", "computer-readable medium", and the like as used herein are broad terms, and are to be given their ordinary and customary meaning to a person of ordinary skill in the art (and are not to be limited to a special or customized meaning), and refer without limitation to media such as, memory storage devices, or storage unit. These, and other forms of computer-readable media, may be involved in storing one or more instructions for use by a processor to cause the processor to perform specified operations. Such instructions, generally referred to as "computer program code" (which may be grouped in the form of computer programs or other groupings), which when executed, enable a computing system to carry out specific functions in accordance with the computer program code.

Continuous Sensor

Embodiments relate to use of analyte sensors that measure a concentration of analyte of interest or a substance indicative of the concentration or presence of the analyte. Such analyte sensors may use any known method, including invasive, minimally invasive, and non-invasive sensing techniques, to provide an output signal indicative of the concentration of the analyte of interest. In some embodiments, an analyte sensor comprises a continuous analyte sensor, for example a subcutaneous, transdermal, or intravascular device. In some embodiments, a glucose sensor can take a plurality of intermittent or periodic measurements. An analyte sensor can use any method of analyte-measurement, including enzymatic, chemical, physical, electrochemical, spectrophotometric, polarimetric, calorimetric, radiometric, or the like. Generally, an analyte sensor can be any sensor capable of determining the level of any analyte in the body, for example glucose, oxygen, lactase, hormones, cholesterol, medicaments, viruses, or the like. It should be understood that the devices and methods described herein can be applied to any device capable of continually, continuously and/or intermittently detecting a concentration of analyte and providing an output signal that represents the concentration of that analyte.

In one embodiment, an analyte sensor is an implantable glucose sensor, such as described with reference to U.S. Pat. No. 6,001,067 and co-pending U.S. Patent Application Publication No. 2005/0027463 entitled, "SYSTEM AND METHODS FOR PROCESSING ANALYTE SENSOR DATA," filed Aug. 1, 2003 and published on Feb. 3, 2005, each of which is incorporated herein by reference in its entirety. In another embodiment, an analyte sensor is a transcutaneous glucose sensor, such as described with reference to U.S. Patent Publication No. 2005/0143635 entitled, "CALIBRATION TECHNIQUES FOR CONTINUOUS ANALYTE SENSOR," filed on Dec. 3, 2004 and published on Jun. 30, 2005. In another embodiment, the continuous glucose sensor comprises a transcutaneous sensor such as described in U.S. Pat. No. 6,565,509 to Say et al., for example. In a further embodiment, a continuous glucose sensor comprises a subcutaneous sensor such as described with reference to U.S. Pat. No. 6,579,690 to Bonnecaze et al. or U.S. Pat. No. 6,484,046 to Say et al., for example. In another embodiment, the continuous glucose sensor comprises a refillable subcutaneous sensor such as described with reference to U.S. Pat. No. 6,512,939 to Colvin et al., for example. In another embodiment, a continuous glucose sensor comprises an intravascular sensor such as described with reference to U.S. Pat. No. 6,477,395 to Schulman et al., for example. In another embodiment, the continuous glucose sensor comprises an intravascular sensor such as described with reference to U.S. Pat. No. 6,424,847 to Mastrototaro et al. All of the above patents and patent publications are incorporated by reference herein in their entireties.

Example Performance Report Systems

FIG. 1 is a diagram illustrating a continuous analyte sensor 10 transmitting intermittent sensor readings 12 (including sensor readings 12A, 12B, 12C, etc.) to a historical sensor data storage 30. The intermittent sensor readings 12 can each comprise sensor data, such as calibrated data, smoothed data, filtered data, and/or transformed data. Depending on the embodiment, the intermittent sensor readings 12 include indications of one or more analyte levels of a host 40 (e.g. such as a blood glucose level of the host 40) and/or any quantity of transformed sensor data, including filtered and/or smoothed sensor data. The intermittent sensor readings may be sensed and transmitted from the continuous analyte sensor 10 on a substantially regular schedule, such as every 3 minutes, 5 minutes, 10 minutes, 30 minutes, or hour, for example, or in response to certain triggers, such as the blood glucose level of the host 40 exceeding a threshold, or in response to a request sent from another device in communication with the analyte sensor. In some embodiments, the frequency of transmitting intermittent sensor readings 12 from the continuous analyte sensor 10 changes based on a current condition of the host 40. For example, the continuous analyte sensor 10 may transmit intermittent sensor readings 12 at a higher frequency when the blood glucose level of the host 40 is outside of a preferred range (e.g., the host 40 is approaching hypoglycemia or hyperglycemia). With the use of a continuous analyte sensor 10, the historical sensor data storage 30 advantageously includes multiple sensor readings for the host 40 covering multiple 24-hour periods, such as from 72 sensor readings (an average of three readings per hour) to 288 sensor readings (an average of 12 readings per hour), or more, for each 24 hour period. This frequency of sensor readings advantageously allows more accurate determination of trends of the host over a period of several hours, days, weeks, or longer.

In the embodiment of FIG. 1, the intermittent sensor readings 12 are stored in the historical sensor data storage 30 so that the sensor data can be accessed by one or more computing devices, such as the host computing device 20, in order to allow the computing devices to analyze the historical sensor data and calculate one or more performance indicators, such as comparison metrics that compare sensor data from two or more analysis time periods. In some embodiments, performance reports, such as tables, charts, graphs, and/or any other user interface that illustrate differences and/or similarities in sensor data between analysis time periods may also be determined based on the historical sensor data stored on the historical sensor data storage 30. For example, comparison of a mean blood glucose level of a host over a first one week period (e.g., based on at least 72 sensor readings per day from a continuous analyte sensor) may be compared to a mean blood glucose level of the host over a second one week period in order to determine a general comparison of how the hosts blood glucose levels changed (overall) between the two one week periods. Comparison of the performance indicators and/or comparison metrics (e.g. the mean blood glucose levels for each of the two weeks) may be displayed in one of multiple performance reports, such a graphs, charts, tables, reports, etc. Performance reports may indicate glucose variability over and/or between more than two time periods, for example, a week-by-week comparison over a month's sensor data (e.g., 4 time periods). For example, a user may select a start and/or end date of an overall analysis time period for analysis (e.g., a last month or last quarter) and then select how many periods in which to divide the analysis time period.

In one embodiment, the continuous analyte sensor 10 includes a communication interface (not shown) for enabling data to be transmitted and/or received over one or more data networks. The data can be transmitted or received wirelessly, through the use of wires, or both. Data transmitted to a receiving device can be first packetized and processed according to one or more standardized network protocols. The communication may accommodate any wired or wireless protocol including, without limitation, USB, FireWire, Ethernet, Gigabit Ethernet, MoCA, radio frequency tuners, modems, ANT, WiFi, Blutooth, WiMax, and/or Infrared Data Association. In this manner, continuous analyte sensor 10 can transmit the intermittent sensor readings 12A and 12B via the communication interface to the historical sensor data storage 30.

Historical sensor data storage 30 can include any type of module adapted to enable digital information, including the intermittent sensor readings 12A and 12B, to be stored, retained, and retrieved. Additionally, historical sensor data storage 30 may comprise any combination of volatile and non-volatile storage devices, including without limitation RAM, DRAM, SRAM, ROM, and/or flash memory. Note also that historical sensor data storage 30 may be organized in any number of architectural configurations, through the use of registers, memory caches, data buffers, main memory, mass storage, and/or removable media, for example. Furthermore, historical sensor data storage 30 need not be a physically separate device, but can reside with sensor 10, host computer 20, or other computing device in communication with sensor 10 or host computer 20.

The host computing device 20 comprises any suitable electronic device for accessing the historical sensor data stored on the historical sensor data storage 30, analyzing at least portions of the historical sensor data, and generating one or more comparison metrics and/or performance reports indicating a performance of the host as a comparison of sensor data from two different analysis time periods (to the host and/or other interested parties, such as a caretaker or medical advisor). For example, in the embodiment of FIG. 1 the host computing device 20 comprises a performance report module 22 that is configured for execution by the host computing device in order to access historical sensor data from a first and a second analysis time period, perform analysis (e.g., mathematical and/or statistical analysis) on the sensor data from each of the analysis time periods, and generate one or more performance indicators that indicate differences in the sample data from the two analysis time periods. The performance report module 22 may be further configured to generate one or more performance reports, such as graphs, charts, tables, etc., that include and/or otherwise illustrate the determined performance indicators, which may be displayed on a display device of the host computing device 20 or other display device. Depending on the embodiment, the analysis time periods may be any time period, such as one day, one week, two weeks, three weeks, one month, two months, three months, six months, one year, or any other time period. Thus, the performance report module 22 provides the host 40 with reports that indicate changes in sensor data over various time periods.

Figure 2:
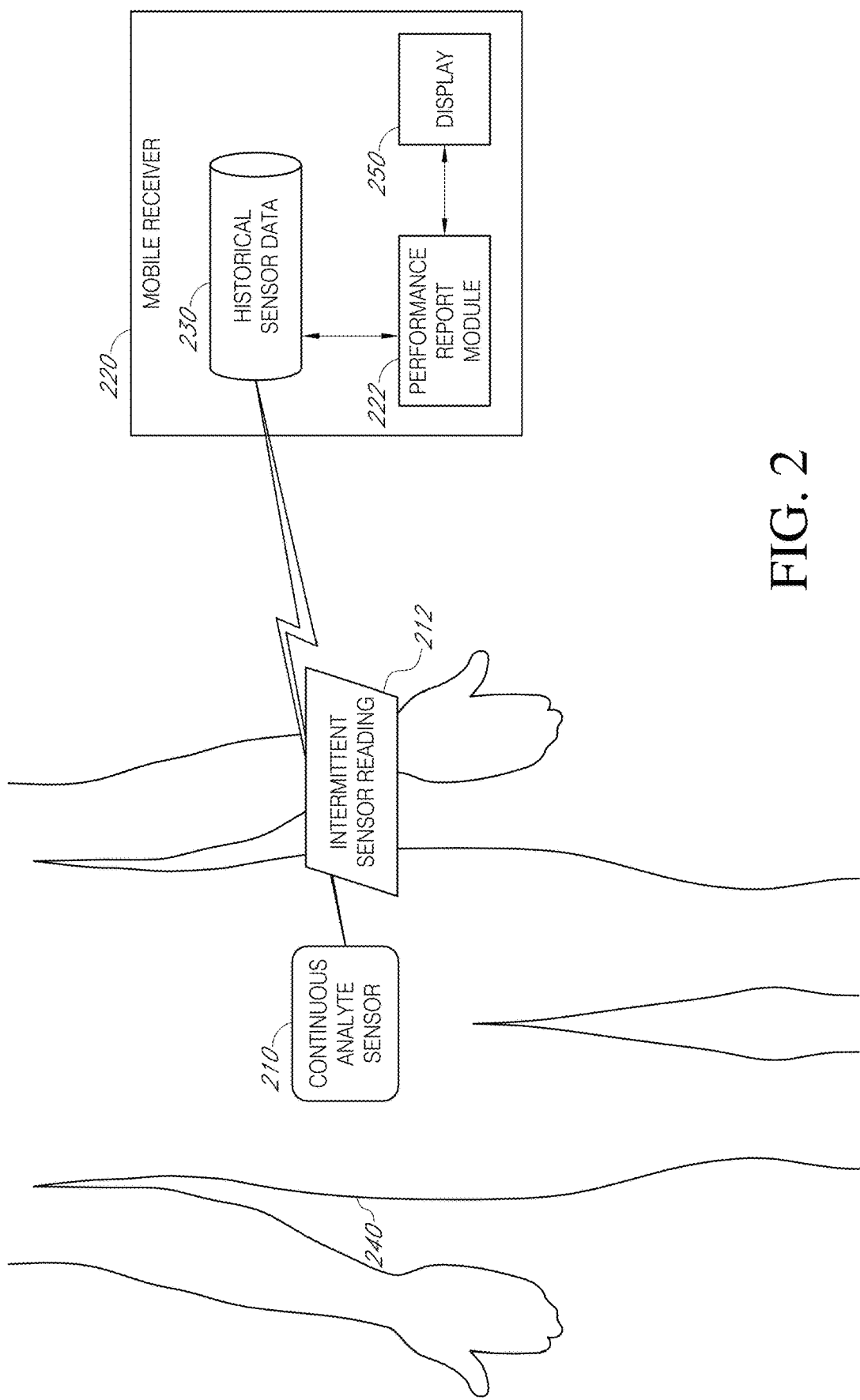
FIG. 2 is a schematic diagram of a performance report system using a mobile receiver in accordance with one embodiment.

FIG. 2 is a diagram illustrating a continuous analyte sensor 210 in communication with a mobile receiver 220 in accordance with one embodiment. The mobile receiver 220 can be a portable receiver that is carried by a host 240, for example. In one exemplary environment, the host 240 has diabetes and the mobile receiver 220 tracks a blood glucose level of the host 240 based on intermittent sensor readings 212 from the continuous analyte sensor 210. (Continuous analyte sensor 210 can be the same sensor as analyte sensor 10 described with reference to FIG. 1.) The mobile receiver 220 can be configured to be worn by the host 240, such as on the wrist of the host 240, or supported by a belt or clip on the host 240. The mobile receiver 220 can comprise a mobile electronic device that includes other functionality, such as a mobile telephone, personal digital assistant, personal computer, smart phone, digital media player, exercise monitoring device, geographic position-tracking device (e.g., GPS) or any other similar device. In one embodiment, mobile receiver 220 includes some or all of the functionality of the host computing device 20 described with reference to FIG. 1.

In the embodiment of FIG. 2, the continuous analytes sensor 210 transmits intermittent sensor readings 212 to the mobile receiver 220, which comprises historical sensor data storage 230 for storing sensor data (e.g. such as volatile and/or nonvolatile memory), including the received intermittent sensor readings 212. Thus, the mobile receiver 220 stores sensor data from the continuous analytes sensor 210 that may be analyzed in order to determine performance indicators and generate performance reports associated with host 240. In one embodiment, historical sensor data storage 230 includes some or all of the functionality of the historical sensor data storage 30 described with reference to FIG. 1.

The mobile receiver 220 can also comprises a performance report module 222 that is configured to determine one or more performance indicators indicating comparisons of sensor data from two or more analysis time periods and to generate one or more performance reports (e.g., user interfaces that are displayable on a display device) that illustrate certain of the performance indicators. The exemplary mobile receiver 220 also includes a display 250 configured to depict the performance indicators and/or certain user interfaces generated by the performance report module 222. In addition, the mobile receiver 220 may include a telemetry module (or other transceiver) that is configured to receive and transmit sensor data and/or performance reports to and from other devices, such as one or more computing devices that may analyze the sensor data and generate performance reports and/or other reports associated with the sensor data. Such devices may transmit generated reports back to the mobile receiver 220 such that the reports can be depicted to be host 240 on the display 250.

Example Generation of Performance Indicators

Figure 3:
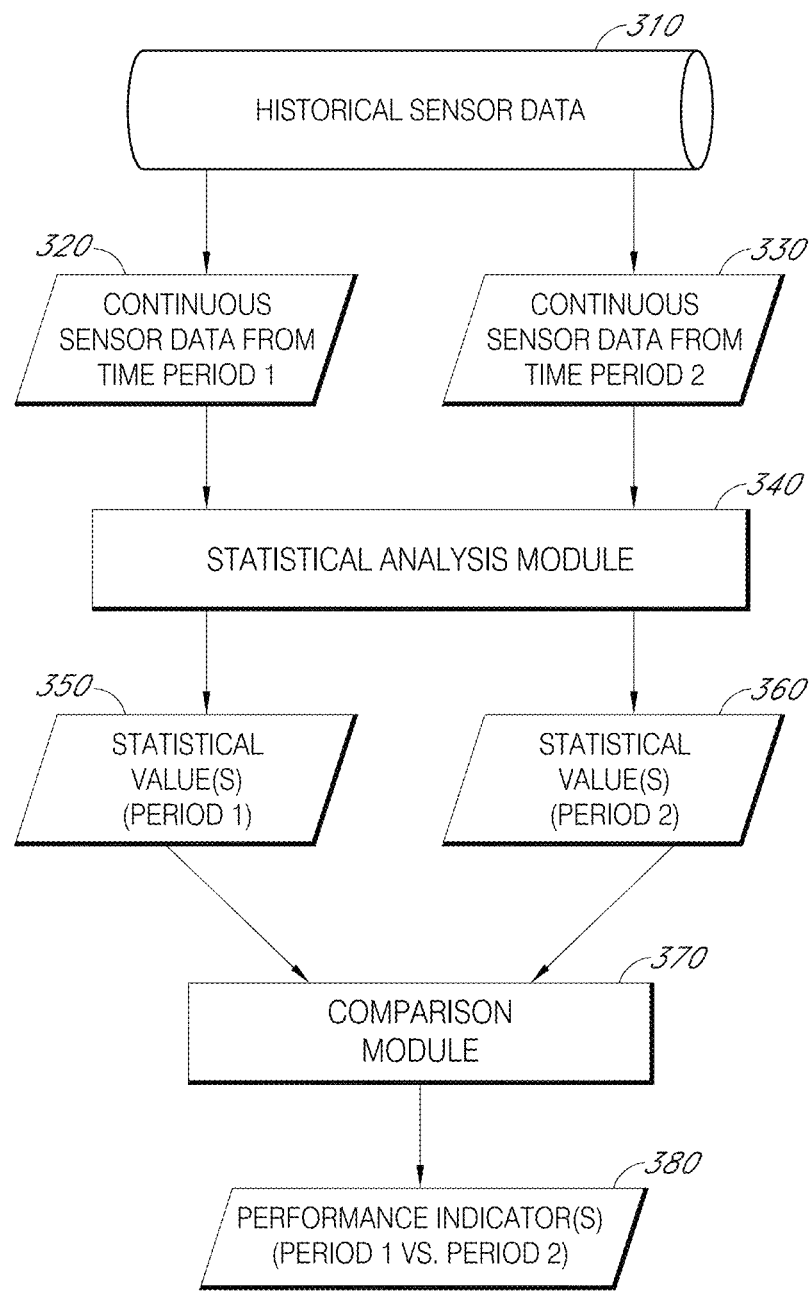
FIG. 3 is a flow diagram illustrating a method of generating performance indicators associated with sample data of a host in accordance with one embodiment.

FIG. 3 is a flow diagram illustrating a method of generating performance indicators associated with sample data of a host in accordance with one embodiment. In the embodiment of FIG. 3, continuous sensor readings from two analysis time periods, such as sequential or nonsequential time periods, are selected for analysis. The sample data from the two analysis time periods is then analyzed to generate one or more performance indicators, which may be displayed as part of one or more of multiple possible performance reports that generally indicate changes in the sensor data of the host from one analysis period to the next analysis period. In some embodiments, sample data from more than two analysis time periods may be selected and analyzed, such that performance indicators are generated from each of the more than two analysis time periods and performance reports that indicate changes in the sensor data and/or performance indicators over the more than two analysis time periods may be generated.

In the example of FIG. 3, the historical sensor data storage 310, which can be data storage 30 or 230, stores sensor data received from a continuous analyte sensor, such as sensor 10 or 210. Depending on the embodiment, the sensor data may span various time periods, such as weeks, months, years, or longer. The historical sensor data may include sensor readings that are received as frequently as every minute, and thus can include multiple readings per hour. As illustrated in FIG. 3, continuous sensor data from analysis time period 320 and continuous sensor data from analysis time period 330 are both transmitted to a statistical analysis module 340. The statistical analysis module 340 can be configured to analyze the sensor data from each of the analysis time periods and generate one or more statistical values associated with the sensor data (e.g., the sensor readings) for each of the time periods. The length of the analysis time periods may also vary. For example, in one embodiment, each of the analysis time periods is one week, while in another embodiment each of the analysis time periods is a quarter of a year. Other analysis time periods can be one or more hours, days, weeks, months, quarters of a year or years. The statistical analysis module 340, which may comprise computer program code that is executed by a computing device, such as the host computing device 20 or the mobile receiver 220 (FIG. 1 or FIG. 2, respectively), generates statistical values 350 based on continuous sensor data from analysis time period 320 and generates statistical values 360 based on continuous sensor data from analysis time period 330. The statistical values for each analysis time period can vary, but generally include one or more indications of glucose variability during the selected time period. The glucose variability may include first, second, or even third order indications of glucose variability. Examples of blood glucose variability include a mean glucose level, a standard deviation of glucose levels during the analysis time period, a trend during the analysis time period, a percentage and/or quantity of days during the analysis time period in which the host was within a target glucose range, a percentage and/or quantity of days within the time period in which the host used the continuous analyte sensor for a minimum time, and any other related statistic.

In the embodiment of FIG. 3, the statistical values 350, 360 associated with the two (or more) selected analysis time periods are received by a comparison module 370 that is configured to compare the statistical values in order to generate one or more performance indicators 380, such as comparison metrics, that are indicative of relationships between the sensor data from the first and second analysis time periods. The performance indicators 380 may include numbers, scores, percentages, trends, averages, grades, ranks, images, graphs, charts, and/or any other indicia that are indicative of differences and/or similarities between the statistical values 350, 360 and/or sensor data 320, 330 associated with respective first and second analysis time periods. The performance indicators may also include comparison metrics, such as one or more overall trends in the improvement (or lack thereof) in a variety of areas for the two or more analysis time periods. Such comparison metrics can be expressed, for example, by analyzing a predetermined, selectable, or changing, quantity of analysis time periods and generating a smoothed or filtered trend of the analysis times periods using one or more statistical parameters.

In one embodiment, target sensor data is used instead of the continuous sensor data 320 or 330. Target sensor data can be indicative of a performance goal and can be provided by a caretaker, such as a physician of the host. For example, a physician may have a particular performance goal for a host and, accordingly may determine target glucose values for that host. Target sensor data—indicative of these target glucose values, for example—may be downloaded to the performance report module 22, 222 (FIGS. 1 and 2) and compared to actual data from the host from a previous analysis time period in order to gauge performance of the host with respect to the target performance goals set by the host's physician.

For example, in the embodiment of FIG. 3, the continuous sensor data 320 may comprise sensor data of the host 40, 240 from a previous one-month period and one month target data provided by the host's physician can be used instead of the continuous sensor data 330. Thus, in this example, when the statistical values and comparison metrics are generated, as described in further detail below, the performance reports and comparison metrics that are generated show the relative performance of the host with respect to the targets provided by the host's physician.

In any of the embodiments discussed herein, target data provided by a caretaker can be used instead of sample data of a host for an analysis time period in order to achieve similar target comparison results. Additionally, multiple analysis time periods, such as three or more, may be analyzed in generating performance reports using target data. Thus, in one embodiment, two analysis time periods comprising host sample data and one analysis time period comprising target data supplied by a physician may be analyzed in generating performance reports for the host.

In one embodiment, performance indicators 380 include and/or initiate display of other information to the host, such as statistical, clinical, expert, and/or therapy recommendations/advice that may be aimed at improving overall glucose control, diabetes management, modified timing, and/or amount of pre-prandial insulin dose information, for example. Such information can be associated with respective criteria, such as criteria associated with one or more statistical values, performance indicators, and/or ranges of these values. Thus, if criteria for a particular clinical/therapy recommendation are met, such as if a particular trend in glucose variability is met by a host, the particular clinical/therapy recommendation may be displayed (or otherwise provided, e.g., audibly spoken to the patient via a speaker on the receiver) to the host. A caretaker, such as a parent, guardian, or doctor, can define performance criteria that define when clinical therapy recommendations or other expert advice are provided to the host. The host can be provided with expert advice, e.g., advice from a doctor of the host, via an avatar that is displayed on a display of the host's receiver in response to one or more of the host's performance indicators matching criteria associated with one or more performance criteria established by the host and/or a caretaker of the host, for example. Thus, a caretaker (e.g., doctor) can upload performance criteria (e.g., including performance criteria that are applied to the one or more performance indicators in order to determine if the host has (or hasn't) met desired performance goals) and provide real-time feedback to the host via the receiver 220 and/or the computing device 20, as well as receive the performance information via upload of the information to the caretaker's computing device.

In one embodiment, one or more performance reports that include the performance indicators 380 are generated for display to the host, such as via the host computing device 20 and/or the mobile receiver 220 of FIGS. 1 and 2, for example.

In one embodiment, the performance report module 22, 222 (FIGS. 1, 2, respectively) comprises the statistical analysis module 340 and/or comparison module 370 discussed with respect to FIG. 3. Thus, the host computing device 20 and/or the mobile receiver 220 may be configured to generate statistical values for each of multiple analysis time periods as well as performance indicators and/or performance reports (e.g., user interfaces) including the performance indicators.

Figure 4:
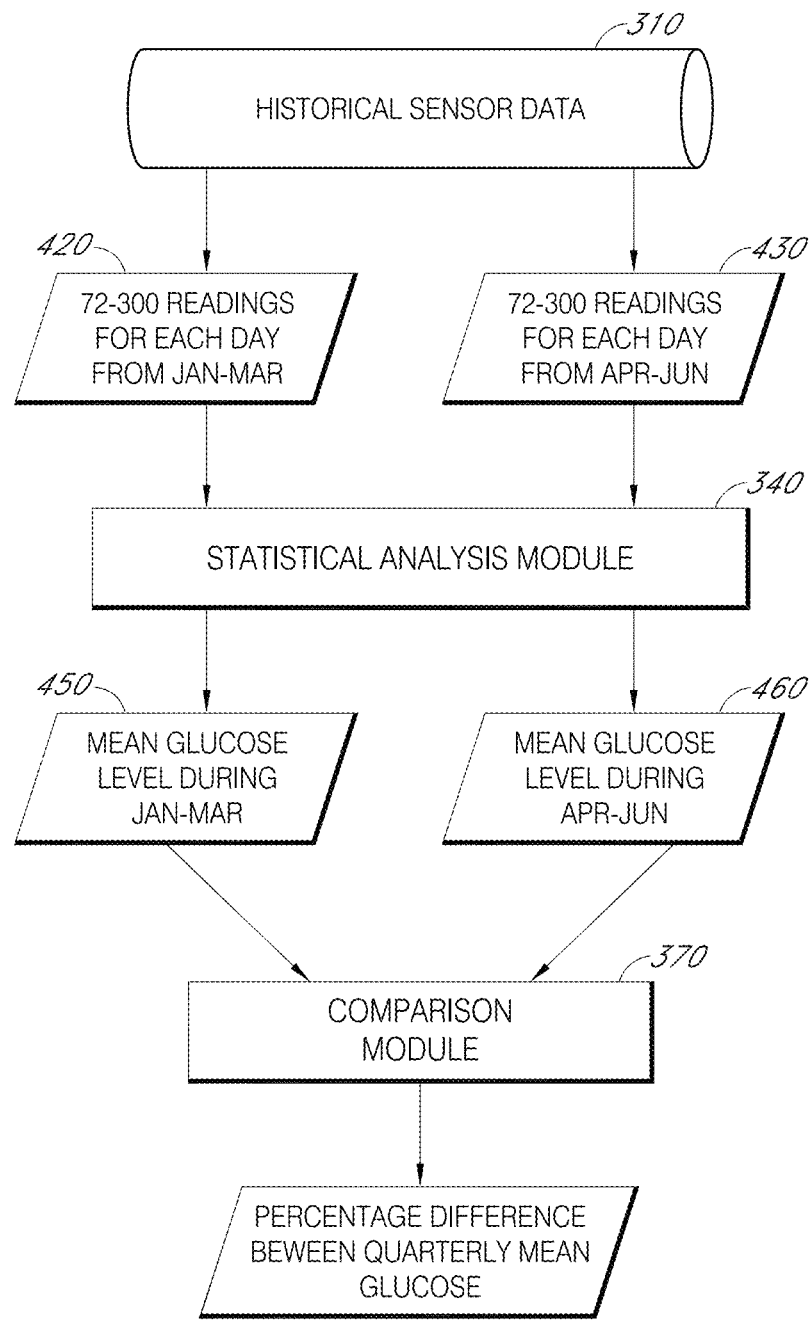
FIG. 4 is a flow diagram illustrating components of FIG. 3, wherein specific exemplary data is shown communicated between the components.

FIG. 4 is a flow diagram illustrating the historical sensor data storage 310, the statistical analysis module 340, and the comparison module 370 of FIG. 3, wherein specific exemplary data is shown communicated between the components. For example, analysis time period data 420 comprises sensor data including 72-300 sensor readings for each day from January to March of a particular year (e.g. 2008) and the analysis time period data 430 comprises sensor data including 72-300 sensor readings for each day from April to June of that same year (e.g., 2008). Thus, in this embodiment the analysis time periods comprise consecutive quarters of a year. In other embodiments, the sensor data may include fewer or additional sensor readings for each 24 hour period. In addition, those of skill in the art will recognize that during certain periods, a host may not use a continuous analytes sensor, or may not properly use a continuous analyte sensor (e.g., the sensor may not be used while on vacation or during exercise or other physical activities, and sensor readings may not be received when the battery of the receiver low or is dead, for example), such that no sensor readings are received. Thus, sensor readings for one or more days (or more) within one of the first or second analysis time periods may include no (or very few) sensor readings. While lack of readings for such a short time period may not be ideal, the embodiments described herein can continue to provide statistical values, performance indicators, and/or performance reports notwithstanding the absence of sensor readings for certain such periods.

In the embodiment of FIG. 4, the statistical analysis module 340 determines a mean glucose level for each of the first and second analysis time periods. Here, mean glucose level 450 represents the sample readings during the January to March analysis time period and mean glucose level 460 represents the sample readings during the April to June analysis time period. In other embodiments, other statistical values may be generated by the statistical analysis module 340. The comparison module 370 receives the mean glucose levels 450, 460 and determines a percentage difference between the quarterly mean glucose levels 450, 460. This percentage difference may be included in one or more performance reports as an indicator of performance of the host from one quarter to the next.

Example Performance Reports

FIGS. 5-8 illustrate exemplary performance reports that include various statistical values and performance indicators in accordance with various embodiments.

FIG. 5 illustrates one exemplary performance report 500 that includes statistical values and performance indicators for each of two analysis time periods, which in this example are months. In particular, the performance report 500 illustrates statistical values associated with a first analysis time period (from January 29 to February 27) in column 510 and statistical values associated with a second analysis period (from February 28 to March 27) in column 520. The performance report 500 also indicates performance indicators indicative of similarities between the statistical values in columns 510 and 520 in column 530. For example, in a row 540, the mean glucose levels of the sensor readings during each of the analysis time periods are provided in columns 510, 520, and a percentage change in the mean glucose levels between the two analysis time periods is indicated in column 530 of row 540. The performance report 500 also includes a column 535 that provides a graphical performance indicator that indicates whether a particular performance indicator is generally positive (e.g., indicated by a smiley face or similar graphic), negative (e.g., indicated by a warning indicator—as illustrated in FIG. 5, a frowney face or similar graphic), or neutral (e.g., indicated by a neutral face or similar graphic). In the illustrative performance report 500, row 542 indicates statistics for the standard deviation of sensor readings during the analysis time periods, wherein in the specific exemplary standard deviations have improved by 2% from the first analysis period to the second analysis period, as illustrated in column 530 of row 542.

The illustrative performance report 500 also indicates in rows 544, 546, 548, 550, a percentage of days the host was in a hypoglycemia range, target range, high range, and hyperglycemia rage, respectively, and includes a change in the number of days that the host was in each of the ranges in column 530 of each respective row. The performance report 500 also includes in row 560 a number of days the analyte sensor was used by this host in each of the two analysis time periods, as well as a change in the number of days the sensor was used by the host in column 530 of row 560.

In one embodiment, the performance indicators of column 535, for example, may be based on a combination of more than one statistical value and/or performance indicator. For example, performance indicators may be provided as combinations of time spent in particular ranges, days/percentage of days that sensors are used, and/or any other performance indicators that are available in order to better provide the host, caretakers, and/or any other interested entity in suitable indicators of performance of the host.

Figures 6A, 6B:
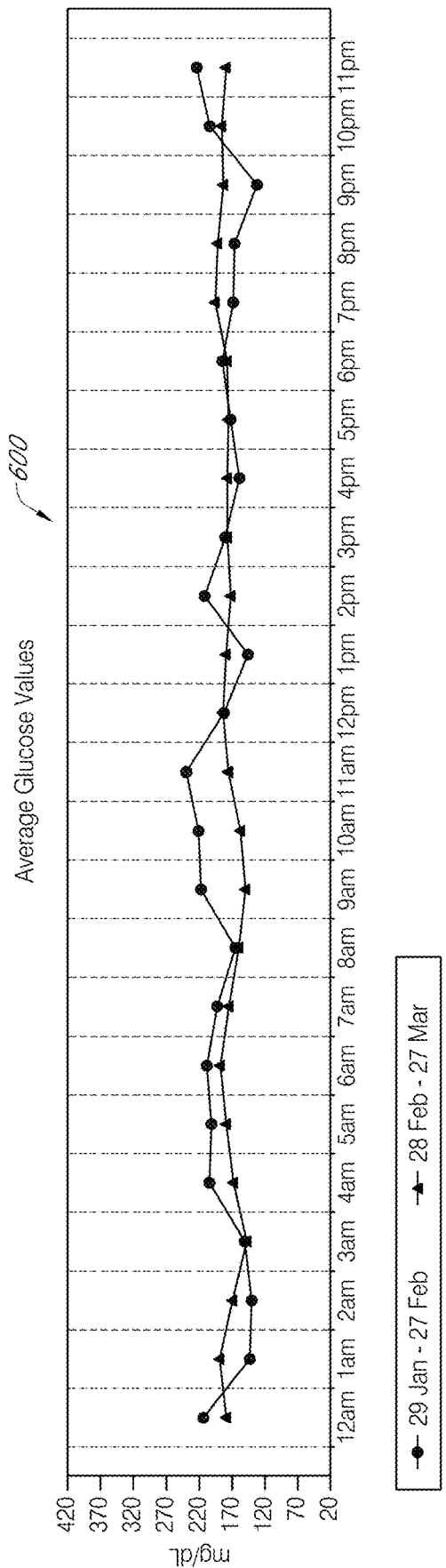

FIG. 6A is an exemplary performance report 600 illustrating sensor readings for each of two analysis time periods in accordance with one embodiment. With reference to FIG. 6A, two line graphs illustrate average blood glucose levels for each hour of a 24 hour period over the course of the relevant analysis time periods, which in this embodiment include a first analysis time period from January 29 to February 27 and a second analysis time period from February 28 to March 27. In FIG. 6B, the same data that is illustrated in the line graphs of FIG. 6A is shown in table format, such that the average blood glucose levels for each one hour period during the relevant time periods are shown in each field. For example, in field 610, the blood glucose level of 214 mg/dL indicates that during the first analysis time period from January 29 to February 27 the host had an average blood glucose level of 214 mg/dL during the hour from 12 am to 12:59 am (which may have included from 5-60 sensor readings per day during that time period). Similarly, the blood glucose level of 145 mg/dL indicates that during the time period from January 29 to February 27 the host had an average blood glucose level of 145 mg/dL during the hour from 1 am to 1:59 am. Each of the fields of the table of FIG. 6B may be associated with multiple sample readings from multiple days, such as 2-20 sample readings per day, for example. In other embodiments, continuous sensor readings may be averaged over shorter or longer time periods, such as periods of 10 minutes, 30 minutes, or two hours, for example.

Figure 7:
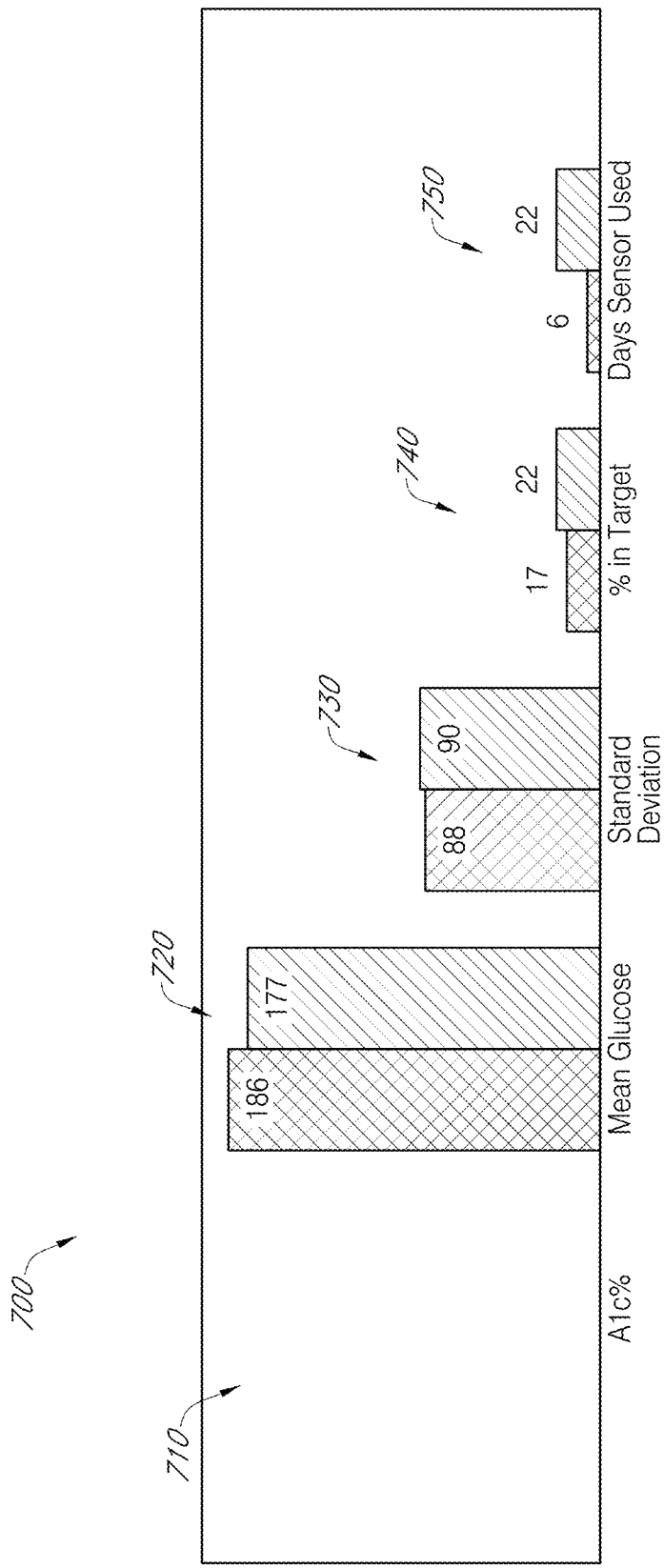

FIG. 7 is an exemplary performance report 700 illustrating a bar graph showing exemplary success metrics from each of the two compared analysis time periods. In the embodiment of FIG. 7, bar graphs for each of the two analysis time periods are provided side-by-side for each of a number of statistical values. Thus, the viewer can easily distinguish a general performance of the host based on differences in the bar graphs for various statistical values. In FIG. 7, the performance report illustrates bar graphs for each of the two analysis time periods including A1c % values 710, mean glucose values 720, standard deviation values 730, percentage in target values 740, and days sensor used values 750. In other embodiments, additional or fewer statistical values may be included in a similar performance report.

Figure 8:
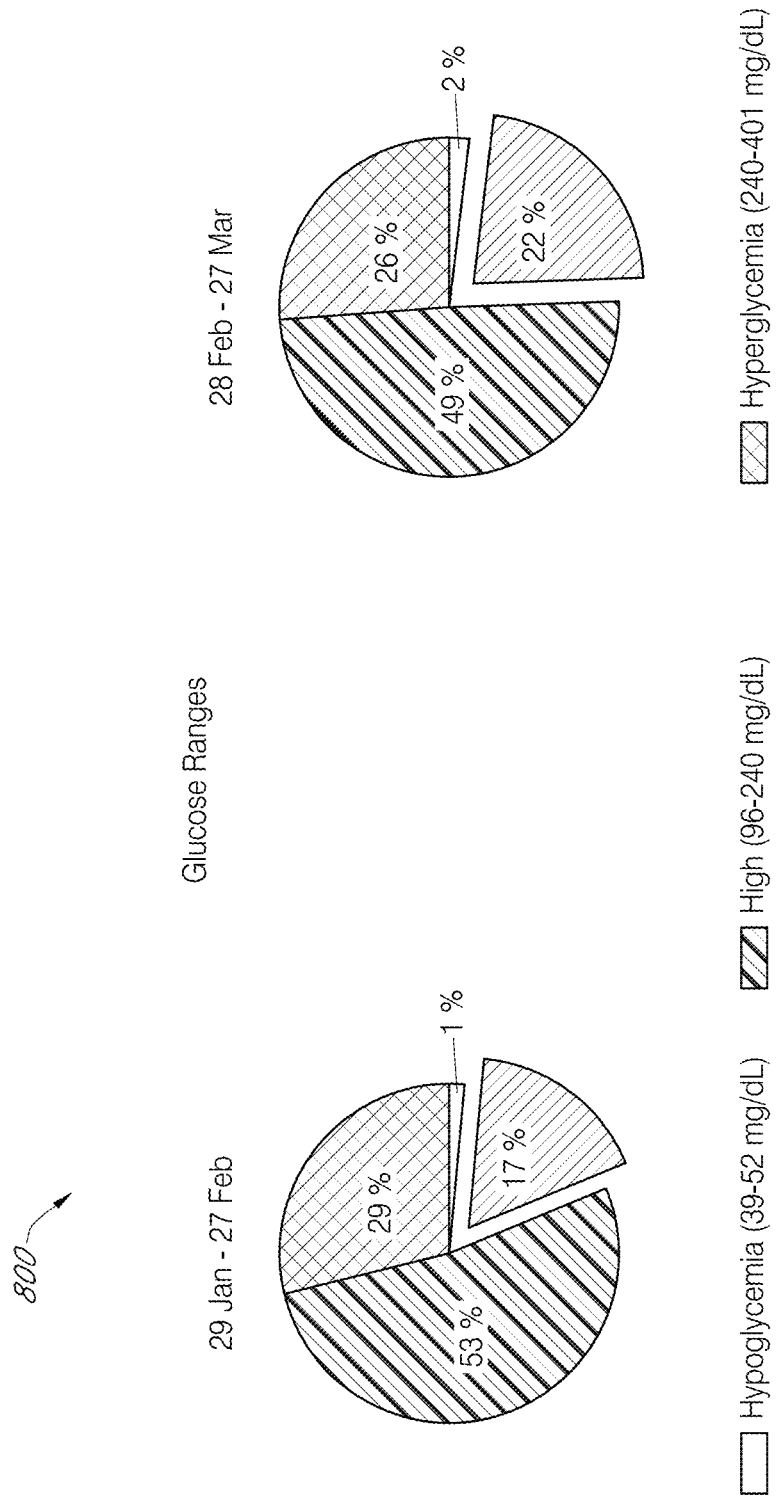

FIG. 8 is an exemplary performance report 800 illustrating pie graphs showing percentage of time that a host was in each of a plurality of predefined blood glucose ranges during each of the two analysis time periods. In this embodiment, the predefined ranges include a hypoglycemia range, a target range, a higher range, and a hyperglycemia range. In other embodiments, the ranges may include fewer or additional ranges. Depending on the embodiment, the ranges may be predefined by a software application and/or may be user-definable, such as by a host, caretaker of a host, or physician. Additionally, the performance report 800 may include a performance indicator, such as a comparison pie graph, that shows a difference between the percentage time in each of the ranges between the two comparison time periods. For example, the graph may illustrate that the host decreased 4% from the first analysis period to the second analysis time period in the amount of time spent in the high range.

Although A1c % values are not indicated in the report 700 or report 800, in one embodiment, a user can input A1c % values—via host computer 20 or mobile receiver 220, for example. In another embodiment, performance report module 22, 222 (FIGS. 1 and 2, respectively) can calculate estimated A1c % values based on historical sensor data stored in historical sensor storage 30, 203, for example. In other words, an estimated A1c % can be calculated based on continuous glucose sensor readings. In either embodiment, the inputted and/or estimated A1c % values can then be illustrated in the performance reports 700 and 800.

There are a myriad of ways an estimated A1c % can be calculated using continuous analyte sensor readings. For example, an estimated A1c % can be calculated based on a magnitude and amount of time that a host's continuous glucose sensor readings fall outside of or inside a predetermined range during an analysis time period. For example, the estimated A1c % can be calculated by integrating the area bounded between a host's glucose level (based on the host's continuous glucose sensor readings during an analysis time period) and upper and/or lower levels of the predetermined range, while the host's glucose level falls outside of the predetermined range. In another example, the A1c % value is based only on a time and magnitude that the host's glucose level, as indicated by the host's continuous glucose sensor readings, exceed a threshold.

An estimated A1c % can be based on other statistical calculations (in addition to or in place of the exemplary integration calculation mentioned above), including one or more of the following: weighting glucose values based the time of the day the glucose values were measured, standard deviation (SD), percentage coefficient of variation (% CV), interquartile range (IQR), mean amplitude of glucose excursion (MAGE), mean of daily differences (MODD), continuous overlapping net glycemic action over an n-hour period (CONGAn), a weighted average of glucose values (MR) (e.g., M100 is M at 100 mg=dL), a measure of quality of glycemic control based on mean and SD (J), the Glycemic Risk Assessment Diabetes Equation (GRADE), the Index of Glycemic Control (IGC), the High Blood Glucose Index (HBGI), the Low Blood Glucose Index (LBGI), the Average Daily Risk Range (ADRR), and percentage of glucose values within specified ranges.

Performance reports can also be based on or include a variety of other statistical information. For example, performance report module 22, 222 can calculate a Glycemic Variability Index (GVI) and generate a performance report that indicates the calculated GVI. In general, the GVI can indicate a quality of glucose control over time based on continuous analyte sensor data.

In one embodiment, the GVI is representative of a magnitude and amount of time that a host's glucose levels fall outside of or inside a predetermined range during an analysis time period. For example, the GVI can be calculated by integrating the area bounded between a host's glucose level over an analysis time period (based on the host's continuous glucose sensor readings) and upper and/or lower levels of the predetermined range, while the host's glucose level falls outside of the predetermined range. The predetermined range can define a range of acceptable glucose concentration levels of the host. The upper and lower thresholds of the range can be set and modified by the host or the host's caretaker or healthcare provider using host computing device 20 or mobile receiver 220, for example.

In one embodiment, the GVI is calculated using additional or other statistical values based on the host's continuous blood glucose sensor readings, including one or more of: weighting glucose values based the time of the day the glucose values were measured, standard deviation (SD), percentage coefficient of variation (% CV), interquartile range (IQR), mean amplitude of glucose excursion (MAGE), mean of daily differences (MODD), continuous overlapping net glycemic action over an n-hour period (CONGAn), a weighted average of glucose values (MR) (e.g., M100 is M at 100 mg=dL), a measure of quality of glycemic control based on mean and SD (J), the Glycemic Risk Assessment Diabetes Equation (GRADE), the Index of Glycemic Control (IGC), the High Blood Glucose Index (HBGI), the Low Blood Glucose Index (LBGI), the Average Daily Risk Range (ADRR), and percentage of glucose values within specified ranges.

The GVI can also be separated into different GVI components to provide a more comprehensive indication of a host's glucose control. In one embodiment, the GVI can include a total GVI component ($GVI_{total}$), a hyperglycemia GVI component ($GVI_{hyper}$) and a hypoglycemia component ($GVI_{hypo}$). The $GVI_{hyper}$ component can be indicative of hyperglycemia control based entirely or substantially in part on sensor values that exceed an upper threshold of a predetermined range (i.e. a hyperglycemia threshold); for example, based on a time and magnitude of continuous sensor readings exceeding the upper threshold. The $GVI_{hypo}$ component can be indicative of hypoglycemia control based entirely or partially on sensor values that fall below a lower threshold of a predetermined range (i.e. a hypoglycemia threshold); for example, based on a time and magnitude of continuous sensor readings falling below the lower threshold. The $GVI_{total}$ can be a sum of the $GVI_{hyper}$ and $GVI_{hypo}$ components. A value for each of these components can be displayed on an electronic device, such as on computing device 20 or receiver 220. In this manner, a user can obtain a better understanding of a host's glucose control because the user can obtain a measure over overall control ($GVI_{total}$), in addition to measures of control in hyperglycemia ($GVI_{hyper}$) and hypoglycemia ($GVI_{hypo}$) ranges.

Example User Interface for Generating Performance Reports

Figure 9:
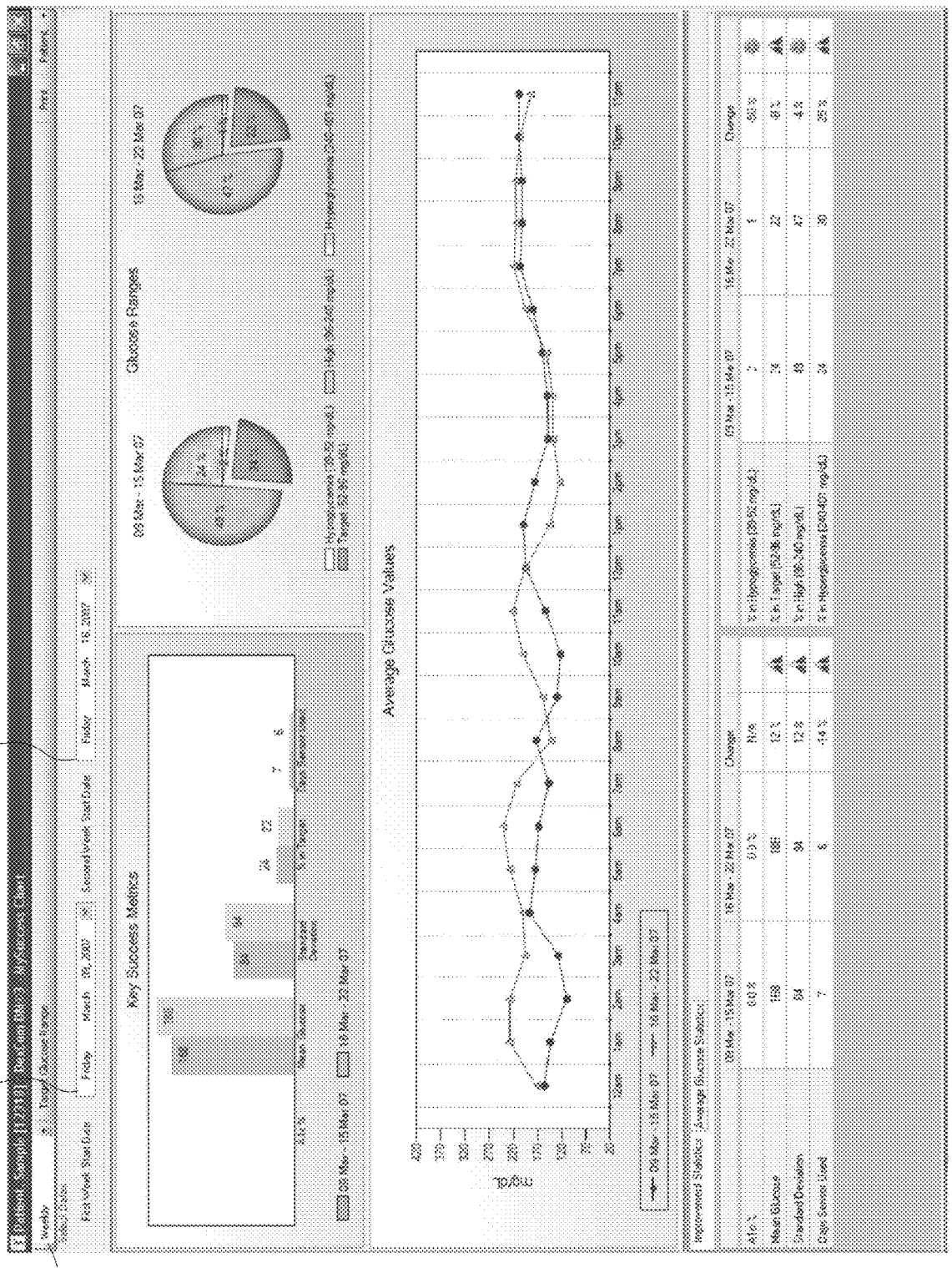
FIG. 9 is an exemplary user interface in accordance with one embodiment.

FIG. 9 is an exemplary user interface 900 in accordance with one embodiment. The user interface 900 can combine performance reports and/or other performance indicators, such as those described above, into a single user interface for display and interaction with a user. The user interface 900 can be implemented using computer program code stored on a computing device used by a host to monitor and track blood glucose levels. For example, the performance report module 22, which may reside on the host computing device 20 and/or other suitable computing device, may comprise computer program code configured to analyze sensor historical data, generate one or more performance reports, and implement the user interface 900 of FIG. 9.

As illustrated in FIG. 9, the user interface 900 includes fields 910 and 920 for inputting respective first and second analysis time periods upon which statistical values, performance indicators, and/or performance reports are desired. For example, the user may input a start date of a first analysis period in the entry field 910 and a start date of a second analysis period in the entry field 920. In the embodiment illustrated in FIG. 9, the default analysis time period is set for one week and the start date of the second analysis period is defaulted to begin immediately after the end date of the first analysis period (i.e. defaulted to have consecutive analysis periods). Thus, in this embodiment, a computing device supporting user interface 900 (e.g., device 20 of FIG. 1) automatically calculates and displays on user interface 900 the end date of the first analysis period and the start date and end date of the second analysis period. The user can also modify the second start date by inputting a different start date in the field 920 of the user interface 900. In this way, a user can compare two analysis periods that are nonconsecutive. Additionally, if a different analysis time period is desired, a user can input a different analysis time period by selecting a desired analysis time period via drop down menu 930. The drop down menu 930 can allow the user to select one of a variety of analysis time periods, such as days, months, quarters, or years, or other custom time periods. After selecting the analysis time period of interest, a computing device supporting user interface 900 (e.g., device 20 of FIG. 1) can access relevant, associated historical sensor data (stored in storage 30, for example) and generate statistical values, performance indicators, and performance reports for display to the host and/or others on a display of a computing device, such as host computing device 20 or mobile receiver 220. For example, the user interface 900 of FIG. 9 includes many of the performance reports illustrated in FIGS. 5-8, discussed above.

It should also be understood that user interface 900 can be modified to display any of the other performance statistics (e.g., performance reports, performance indicators, and/or statistical values based on sensor readings) described herein. In addition, more than two time analysis periods can be selected and displayed on user interface 900. Furthermore, the user interface 900 can be modified to display performance reports that compare multiple analysis time periods with target sensor data.

In one embodiment, performance statistics generated by the computing device 20 and/or mobile receiver 220 may be transmitted to a physician's computing device, personal health records system, and/or other networked health record system. The performance statistics can be transmitted with or without the underlying continuous sensor readings on which the performance statistics are based. In this manner, the need/desire for transmitting all of the continuous sensor readings to a remote device, e.g. a central storage device accessible by the host's physician, may be reduced, because the performance statistics can provide all of the information desired by the physician. For example, if the physician receives a performance report showing how the host's glucose variability has changed month over month and/or quarter over quarter, the physician may not be as interested in viewing, or may not need to view, the individual glucose readings generated from the host's continuous analyte sensor 10, 210 (FIGS. 1 and 2), because the performance report may provide all of the information needed by the physician.

In one embodiment, a report module (not shown) generates a user interface that may be used by a caretaker, such as a doctor, in order to allow the caretaker access to sensor data from multiple hosts and, accordingly, to statistical values, performance indicators, and performance reports for multiple host. Accordingly, such a user interface may allow the physician to view comparisons of performance across multiple selectable population groups. For example, a user interface may be configured to allow a caretaker to select patients based on any one or more demographic (or other) criteria, such as age, gender, etc. Thus, the caretaker may compare the performance of all male patients between the ages of five and fifteen, comparing the period from December-March to July-August, and request a certain set of performance indicators and/or performance reports. For example, the physician may request that performance indicators indicating percentage of time in each of certain ranges and percentage of time the sensors are used are included in performance reports. Accordingly, the report module provides the caretaker with a broader based performance report that may be used to provide therapy recommendations to patients, for example.

In one embodiment, the user interface 900 is capable of automatically recognizing another other electronic device upon connection with the other device. The connection can be either a wireless or wire connection. In this manner, a user does not have to perform any additional actions to tell the either device that the other device is there. These functions can be accomplished using Plug and Play (PnP) or Universal Plug and Play (UPnP) protocols, both of which were developed by Microsoft Corporation. As a non-limiting example, the user interface 900, incorporated into a hand-held mobile device, for example, can automatically install on a computing device, such as host computing device 20 or mobile receiver 220, obtain historical sensor data and/or generate a performance report based on the historical sensor data, upon connection of the user interface 900 with another electric device.

Example Method of Generating Performance Reports

Figure 10:
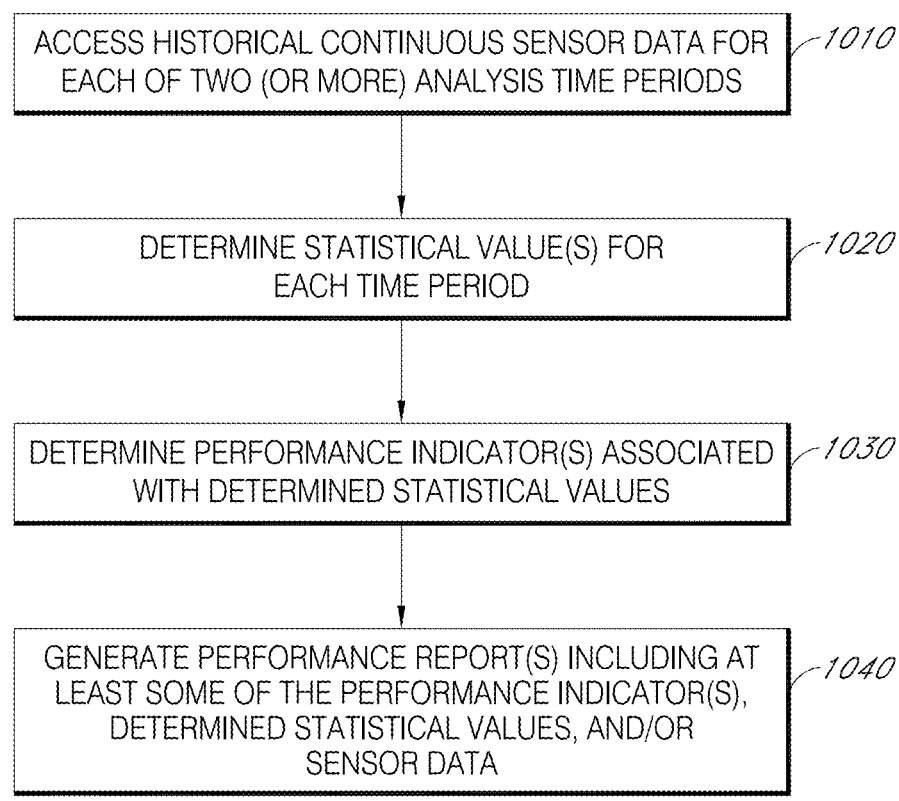
FIG. 10 is a flowchart illustrating a method of generating performance reports indicating performance indicators between continuous sensor data from two or more analysis time periods in accordance with one embodiment.

FIG. 10 is a flowchart illustrating a method of generating performance reports indicating performance indicators between continuous sensor data from two or more analysis time periods in accordance with one embodiment. The various tasks performed in connection with the method of FIG. 10 may be implemented by software, hardware, firmware, a computer-readable medium storing computer executable instructions for performing the process method, or any combination thereof. In addition, the various tasks performed in connection with the method of FIG. 10 may be performed by any suitable computing device, such as the host computing device 20 of FIG. 1, the mobile receiver 220 of FIG. 2, and/or any other suitable computing device. For ease of convenience, the method of Figured 10 may be described from time-to-time with respect to the host computing device 20; however, any reference to the host computing device 20 should be construed to cover any other suitable computing device, including mobile receiver 220. Furthermore, a task associated with a block may be performed by one computing device while other tasks associated with the same block or other blocks may be performed by other computing device(s). Depending on the embodiment, the method of FIG. 10 may include fewer or additional blocks and the blocks may be performed in a different order than is described and illustrated in FIG. 10.

Beginning in block 1010, the host computing device 20 accesses historical continuous sensor data for each of two (or more) analysis time periods. For example, the host computing device 20 may access historical sensor data storage 30 that stores continuous sensor readings for a period of weeks, months, years, or mores. The historical sensor data can include multiple sensor readings per hour, such as more than 72 sensor readings per 24 hour period from a continuous analyte sensor. The historical sensor data for the analysis time periods may be stored local to the host computing device 20, e.g. on a hard drive or optical drive of the computing device, or may be accessed via one or more network connections, e.g., via a local area connections to a server that stores the data.

Moving to block 1020, the host computing device 20 determines one or more statistical values for each of the analysis time periods. The calculated statistical values may include, for example, one or more indications of glucose variability, such as mean glucose levels, standard deviation of glucose levels during the analysis time period, percentage and/or quantity of days during the analysis time period in which the host was within a target glucose range, a hyperglycemic range, a hypoglycemic range, and/or any other custom defined range, a percentage and/or quantity of days within the time period in which the host used the continuous analyte sensor for a minimum time, and any other related statistic.

Next, in block 1030 the host computing device 20 determines one or more performance indicators that indicate differences and/or similarities between the statistical values and/or sensor data of the two or more analysis time periods. The performance indicators may include comparison metrics, such as numbers, scores, percentages, trends, averages, grades, ranks, images, graphs, charts, and/or any other indicia that are indicative of differences and/or similarities between the statistical values deterring in block 1020.

Moving to block 1040, the host computing device generates one or more performance reports, such as interactive user interfaces, tables, charts, graphs, or any other reports that are illustrative of differences and/or similarities in the continuous sensor readings from the analysis time periods. The performance reports may include reports such as those illustrated in FIGS. 5-9, for example, and/or any other performance report. The performance reports may then be displayed on a user interface of a computing device, such as the user interface 900.

Figure 11:
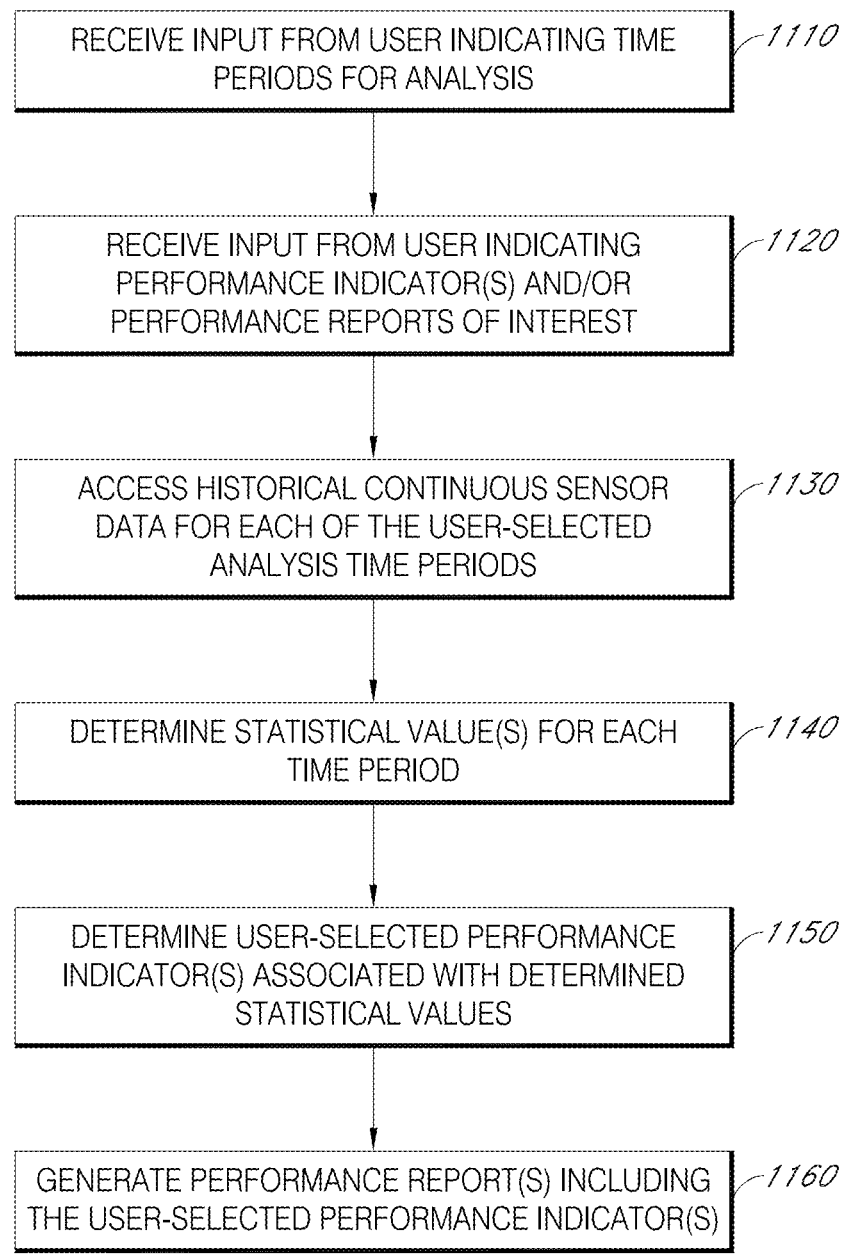
FIG. 11 is a flowchart of a method of receiving user input for generating customized performance reports in accordance with one embodiment.

FIG. 11 is a flowchart of a method of receiving user input for generating customized performance reports, wherein the performance reports include performance indicators indicating comparisons between continuous sensor data from two or more analysis time periods, in accordance with one embodiment. The various tasks performed in connection with the method of FIG. 11 may be implemented by software, hardware, firmware, a computer-readable medium storing computer executable instructions for performing the process method, or any combination thereof. In addition, the various tasks performed in connection with the method of FIG. 10 may be performed by any suitable computing device, such as the host computing device 20 of FIG. 1, the mobile receiver 220 of FIG. 2, and/or any other suitable computing device. For ease of convenience, the method of FIG. 11 may be described from time-to-time with respect to the host computing device 20; however, any reference to the host computing device 20 should be construed to cover any other suitable computing device. Furthermore, a task associated with certain of the blocks may be performed by one computing device while other tasks associated with the same or other blocks may be performed by other computing device(s). Depending on the embodiment, the method of FIG. 11 may include fewer or additional blocks and the blocks may be performed in a different order than is described and illustrated in FIG. 11.

Beginning in block 1110, a user, such as the host 40, doctor, or caretaker, provide the analysis time periods that are to be analyzed in performance reports. For example, a host executing the performance report module 22 on the host computing device 20 may be presented with a user interface, such as the user interface of FIG. 9, wherein the host can select the analysis time period via one or more interface controls. As noted above with reference to FIG. 9, the user interface 900 includes interface controls that allow selection of a default analysis time periods (e.g., via drop down menu 930) and selection of a start date for the first analysis time period (e.g., in field 910), as well as a start date for the second analysis time period (e.g., in field 920). In one embodiment, selection of the analysis time periods is provided via a web accessible user interface.

Next, in block 1120 the user optionally provides an indication of one or more performance indicators and/or performance reports of interest. For example, one user may want to see a performance report indicating percentage differences of times in which the host was in each of three target blood glucose ranges in two consecutive quarters, while another user may want to see a performance report indicating percentage differences in hours that sensor readings were received from one week to the next over a period of several weeks. In certain embodiments, one or more default performance indicators are preselected and will be determined unless they are deselected by the user.

Moving to block 1130, the historical sensor data associated with the host during the analysis time periods is accessed. As noted above with reference to block 1010, such data may be accessed either local to the host computing device or remote to the host computing device via one or more network connections. Advantageously, the historical sensor data for each of the selected analysis periods includes multiple sensor readings, such as from 72-288 sensor readings, per 24 hour period.

In block 1140, the host computing device determines one or more statistical values for each of the user-selected analysis time periods. The calculated statistical values may include, for example, one or more of various indications of glucose variability.

Next, in block 1150, one or more user-selected performance reports are generated including the user-selected performance indicators and/or other determined statistical values. For example, performance reports may be delivered to the user via a web interface, e.g., via a web browser, or via a stand-alone software application. Advantageously, the performance reports illustrate differences and/or similarities in sensor data for extended periods of time (e.g., comparisons of consecutive weeks, months, or quarters).

Note that one or more of the functions described in any of the above embodiments can be performed by firmware stored in a computer-readable storage medium and executed by a processor of computing device 20 or receiver 220. The firmware can also be stored and/or transported within any computer-readable storage medium for use by or in connection with an instruction execution system, apparatus, or device, such as a computer-based system, processor-containing system, or other system that can fetch the instructions from the instruction execution system, apparatus, or device and execute the instructions.

While various embodiments of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can be applied, alone or in some combination, to one or more of the other embodiments of the disclosure, whether or not such embodiments are described, and whether or not such features are presented as being a part of a described embodiment. Thus the breadth and scope of the present disclosure should not be limited by any of the above-described exemplary embodiments.

It will be appreciated that, for clarity purposes, the above description has described embodiments with reference to different functional units. However, it will be apparent that any suitable distribution of functionality between different functional units may be used without detracting from the invention. For example, functionality illustrated to be performed by separate computing devices may be performed by the same computing device. Likewise, functionality illustrated to be performed by a single computing device may be distributed amongst several computing devices. Hence, references to specific functional units are only to be seen as references to suitable means for providing the described functionality, rather than indicative of a strict logical or physical structure or organization.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' including but not 'limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of analyzing continuous analyte sensor data associated with a host, wherein the continuous analyte sensor data is representative of glucose levels of the host, the method comprising:

providing, on a user interface, one or more user interface features for a first analysis time period and a second analysis time period to be selected through user interaction with the one or more user interface features;

receiving, through the user interface, a user selection indicative of the first analysis time period and the second analysis time period, in response to the user interaction with the one or more user interface features, wherein the first analysis time period and the second analysis time period are nonconsecutive time periods;

based on the user selection, accessing a first plurality of blood glucose readings associated with the host for the first analysis time period, wherein each of the first plurality of blood glucose readings is indicative of a blood glucose level of the host at a respective time during the first analysis time period;

based on the user selection, accessing a second plurality of blood glucose readings associated with the host for the second analysis time period, wherein each of the second plurality of blood glucose readings is indicative of a blood glucose level of the host at a respective time during the second analysis time period;

determining a glucose variability metric for each of the first and the second analysis time periods, the glucose variability metric indicating a level of glucose variability in the respective plurality of blood glucose readings for the respective analysis time period;

comparing the glucose variability metrics of the first and the second analysis time periods;

determining whether levels of glucose variability are improving over time between the first and the second analysis time periods based on the comparing; and generating a performance report indicating a relationship between the first plurality of blood glucose readings and the second plurality of blood glucose readings, wherein the performance report includes a first non-numerical performance indicator when the levels of glucose variability indicate an improvement between the first and the second analysis time periods, and a second non-numerical performance indicator when the levels of glucose variability indicate a lack of improvement between the first and the second analysis time periods.

2. The method of claim 1, wherein the performance report further indicates a relationship between the first and the second plurality of blood glucose readings and target sensor data.

3. The method of claim 2, wherein the target sensor data comprises target glucose values determined based on a performance goal for the host.

4. The method of claim 1, further comprising:
initiating transmission of clinical feedback to the host in response to determining that the relationship between the first and the second plurality of blood glucose readings meets criteria indicative of providing the host with clinical feedback.

5. The method of claim 1, wherein the first and the second plurality of blood glucose readings comprise more than 72 blood glucose readings for each 24 hour period of an at least one week period.

6. The method of claim 1, further comprising transmitting the performance report to a caretaker computing device.

7. The method of claim 1, wherein the nonconsecutive time periods are nonconsecutive quarters of a year.

8. The method of claim 1, wherein the glucose variability metric of the respective analysis time period comprises one or more of a mean glucose level, a standard deviation of blood glucose readings during the respective analysis time period, a trend during the respective analysis time period, a percentage and/or quantity of days within the respective time period in which the host used the continuous analyte sensor for a minimum time, or combinations thereof.

9. The method of claim 1, wherein the first non-numerical performance indicator is a positive graphic, and the second non-numerical performance indicator is a negative graphic.

10. The method of claim 1, wherein the performance report further comprises a third non-numerical performance indicator when the levels of glucose variability are substantially unchanged.

11. The method of claim 10, wherein the third non-numerical performance indicator is a neutral graphic.

* * * * *